(12) United States Patent
Zapol et al.

(10) Patent No.: US 10,758,569 B2
(45) Date of Patent: Sep. 1, 2020

(54) HETEROARYL DISULFIDE COMPOUNDS AS ALLOSTERIC EFFECTORS FOR INCREASING THE OXYGEN-BINDING AFFINITY OF HEMOGLOBIN

(71) Applicants: The General Hospital Corporation, Boston, MA (US); Donald B. Bloch, Boston, MA (US)

(72) Inventors: Warren M. Zapol, Cambridge, MA (US); Kenneth D. Bloch; Akito Nakagawa, Cambridge, MA (US); Francine E. Lui, Toronto (CA); Revital Freedman, Brookline, MA (US)

(73) Assignee: The General Hospital Corporation, Boston, MA (US)

( * ) Notice: Subject to any disclaimer, the term of this patent is extended or adjusted under 35 U.S.C. 154(b) by 841 days.

(21) Appl. No.: 15/111,149

(22) PCT Filed: Jan. 13, 2015

(86) PCT No.: PCT/US2015/011118
§ 371 (c)(1),
(2) Date: Jul. 12, 2016

(87) PCT Pub. No.: WO2015/106240
PCT Pub. Date: Jul. 16, 2015

(65) Prior Publication Data
US 2016/0331782 A1    Nov. 17, 2016

Related U.S. Application Data

(60) Provisional application No. 61/926,608, filed on Jan. 13, 2014.

(51) Int. Cl.
| A61K 31/4196 | (2006.01) |
| A61K 35/18 | (2015.01) |
| A61K 31/4155 | (2006.01) |
| A61K 31/4178 | (2006.01) |
| A61K 31/4192 | (2006.01) |
| A61K 31/427 | (2006.01) |
| A61K 31/433 | (2006.01) |
| A61K 31/4015 | (2006.01) |
| A61K 31/42 | (2006.01) |
| A61K 31/352 | (2006.01) |
| A61K 31/525 | (2006.01) |
| A61K 31/198 | (2006.01) |
| A61K 31/17 | (2006.01) |
| A61K 31/167 | (2006.01) |
| A61K 33/30 | (2006.01) |
| A61K 31/381 | (2006.01) |
| A61K 31/41 | (2006.01) |

(Continued)

(52) U.S. Cl.
CPC ............ *A61K 35/18* (2013.01); *A61K 31/167* (2013.01); *A61K 31/17* (2013.01); *A61K 31/198* (2013.01); *A61K 31/352* (2013.01); *A61K 31/381* (2013.01); *A61K 31/4015* (2013.01); *A61K 31/41* (2013.01); *A61K 31/4155* (2013.01); *A61K 31/4178* (2013.01); *A61K 31/4192* (2013.01); *A61K 31/4196* (2013.01); *A61K 31/42* (2013.01); *A61K 31/422* (2013.01); *A61K 31/427* (2013.01); *A61K 31/433* (2013.01); *A61K 31/444* (2013.01); *A61K 31/525* (2013.01); *A61K 33/30* (2013.01); *C07D 231/18* (2013.01); *C07D 233/86* (2013.01); *C07D 249/04* (2013.01); *C07D 249/12* (2013.01); *C07D 249/14* (2013.01); *C07D 257/04* (2013.01); *C07D 261/10* (2013.01); *C07D 277/36* (2013.01); *C07D 285/08* (2013.01); *C07D 285/125* (2013.01); *C07D 285/135* (2013.01); *C07D 333/40* (2013.01); *C07D 401/14* (2013.01); *C07D 405/14* (2013.01); *C12N 5/0641* (2013.01)

(58) Field of Classification Search
CPC .......................... A61K 31/155; A61K 31/4196
See application file for complete search history.

(56) References Cited

U.S. PATENT DOCUMENTS

| 5,028,716 A | 7/1991 | Iwata et al. |
| 5,780,498 A | 7/1998 | Saika et al. |

(Continued)

FOREIGN PATENT DOCUMENTS

| CN | 102775360 | 11/2012 |
| EP | 126012 | * 11/1984 |

(Continued)

OTHER PUBLICATIONS

Beuzard et al. EP 126012, 1984.*

(Continued)

*Primary Examiner* — Rei Tsang Shiao
(74) *Attorney, Agent, or Firm* — Fish & Richardson P.C.

(57) ABSTRACT

This invention relates to compounds of Formula I: (Formula I), and pharmaceutically acceptable salt thereof, which are allosteric effectors that increase the oxygen-being affinity of hemoglobin, which are useful in the treatment of sickle cell disease, high altitude tissue hypoxia, and other conditions.

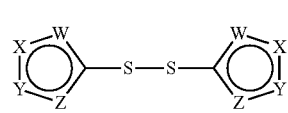

24 Claims, 11 Drawing Sheets

(51) Int. Cl.
| | |
|---|---|
| A61K 31/422 | (2006.01) |
| A61K 31/444 | (2006.01) |
| C07D 231/18 | (2006.01) |
| C07D 233/86 | (2006.01) |
| C07D 249/04 | (2006.01) |
| C07D 249/12 | (2006.01) |
| C07D 249/14 | (2006.01) |
| C07D 257/04 | (2006.01) |
| C07D 261/10 | (2006.01) |
| C07D 277/36 | (2006.01) |
| C07D 285/08 | (2006.01) |
| C07D 285/125 | (2006.01) |
| C07D 285/135 | (2006.01) |
| C07D 333/40 | (2006.01) |
| C07D 401/14 | (2006.01) |
| C07D 405/14 | (2006.01) |
| C12N 5/078 | (2010.01) |

(56) References Cited

U.S. PATENT DOCUMENTS

| | | |
|---|---|---|
| 8,835,464 B2 | 9/2014 | Sun et al. |
| 2012/0322722 A1 | 12/2012 | Robinson et al. |

FOREIGN PATENT DOCUMENTS

| | | |
|---|---|---|
| EP | 0381439 | 8/1990 |
| WO | 1995/011673 | 5/1995 |
| WO | WO 2002/000196 | 1/2002 |
| WO | WO 2006/034327 | 3/2006 |
| WO | WO2013/006631 | 1/2013 |

OTHER PUBLICATIONS

Beuzard et al. claims of EP126012, 1984.*
Beuzard et al. CAS:102,119633, 1985.*

Extended European Search Report in Application No. 15734889.7, dated May 17, 2017, 6 pages.
International Search Report and Written Opinion dated Apr. 8, 2015 in International Application No. PCT/US 15/11118, 13 pgs.
Khanna et al., "Synthesis of various S-S linked symmetric bisazaheterocycles: A Review," Mini-Reviews in Organic Chemistry, 2013, vol. 10, pp. 268-280.
Nakagawa et al, "Identification of a Small Molecule that Increases Hemoglobin Oxygen Affinity and Reduces SS Erythrocyte Sickling," Chemical Biology, Jul. 25, 2014, vol. 9, pp. 2318-2325.
Garel, et al. "Binding of 21 Thiol Reagents to Human Hemoglobin in Solution and Intact Cells," Eur. J. Biochem. 123, 513-519 (1982).
Villela, et al. "Microcirculatory Effects of Changing Blood Hemoglobin Oxygen Affinity During Hemorrhagic Shock Resuscitation in An Experimental Model," Shock, 31(6):645-652 (2009).
Eaton et al., "Survival at extreme altitude: protective effect of increased hemoglobin-oxygen affinity," Science, 1974, 183: 743-744.
Hayashi et al., "An enzymic reduction system for metmyoglobin and methemoglobin, and its application to functional studies of oxygen carriers," Biochemica et Biophysica Acta, Jun. 1973, 310: 309-316.
International Preliminary Report on Patentability in International Application No. PCT/US2015/011118, dated Jul. 19, 2016, 6 pages.
International Search Report and Written Opinion dated Jun. 24, 2015 in International Application No. PCT/US 15/11125, 17 pgs.
Kilgore et al., "RSR13, a Synthetic Allosteric Modifier of Hemoglobin, Improves Myocardial Recovery Following Hypothermic Cardiopulmonary Bypass," Circulation, 1999, vol. 100, pp. II-351-II-356.
Protein Data Bank, 4L7Y, "Deoxygenated Hb in complex with the allosteric effectors, IRL2500 and 2,3-DPG," 2013, retrieved on Feb. 24, 2017, http://www.rcsb.org/pdb/explore.do?structureId=4L7Y, 2 pages.
Vichinsky et al., "Overview of the clinical manifestations of sickle cell disease," 2014, 1-25.
Yu et al., "Diabetes augments and inhaled nitric oxide prevents the adverse hemodynamic effects of transfusing syngeneic stored blood in mice," Transfusion. Jul. 2012 ; 52(7); pp. 1410-1422.

* cited by examiner

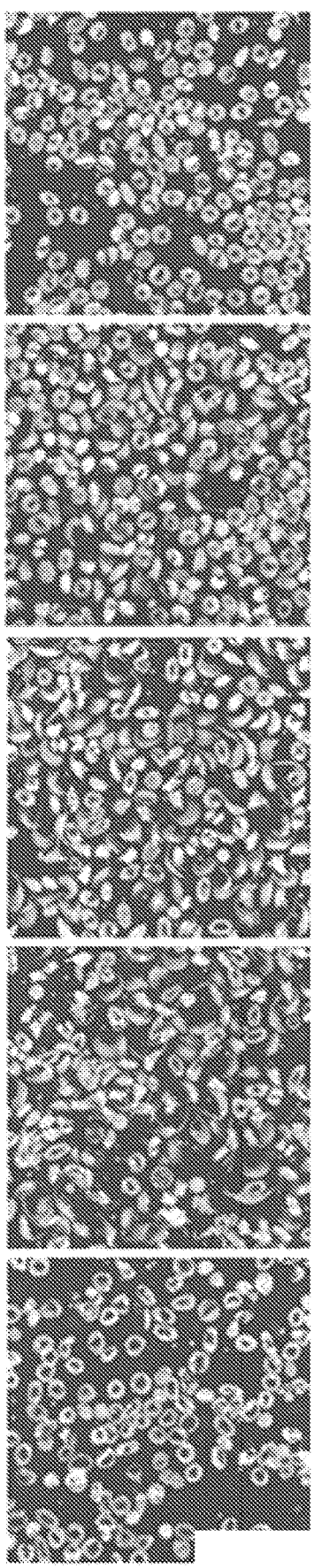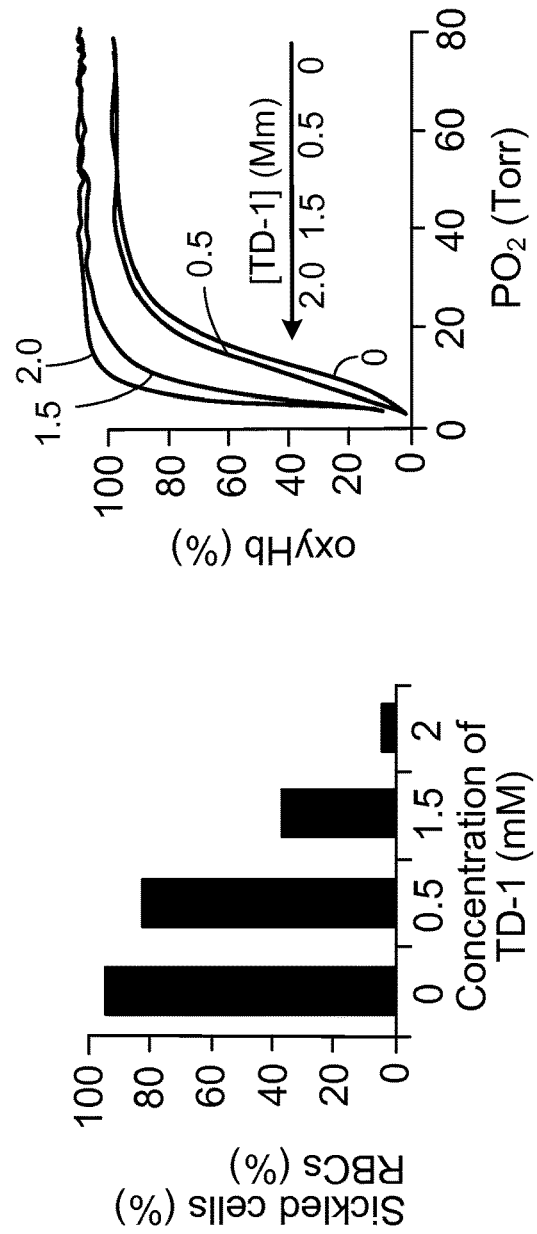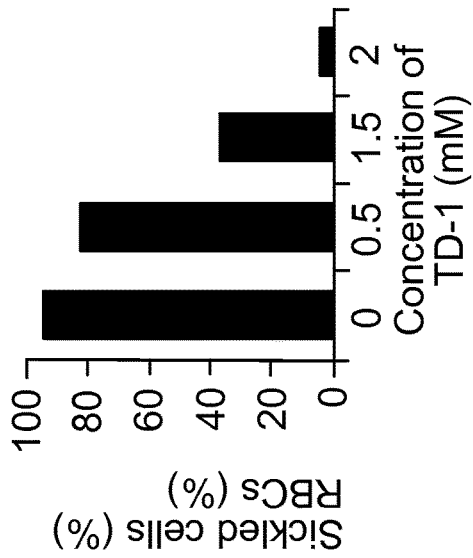

** Hemolysis was observed.

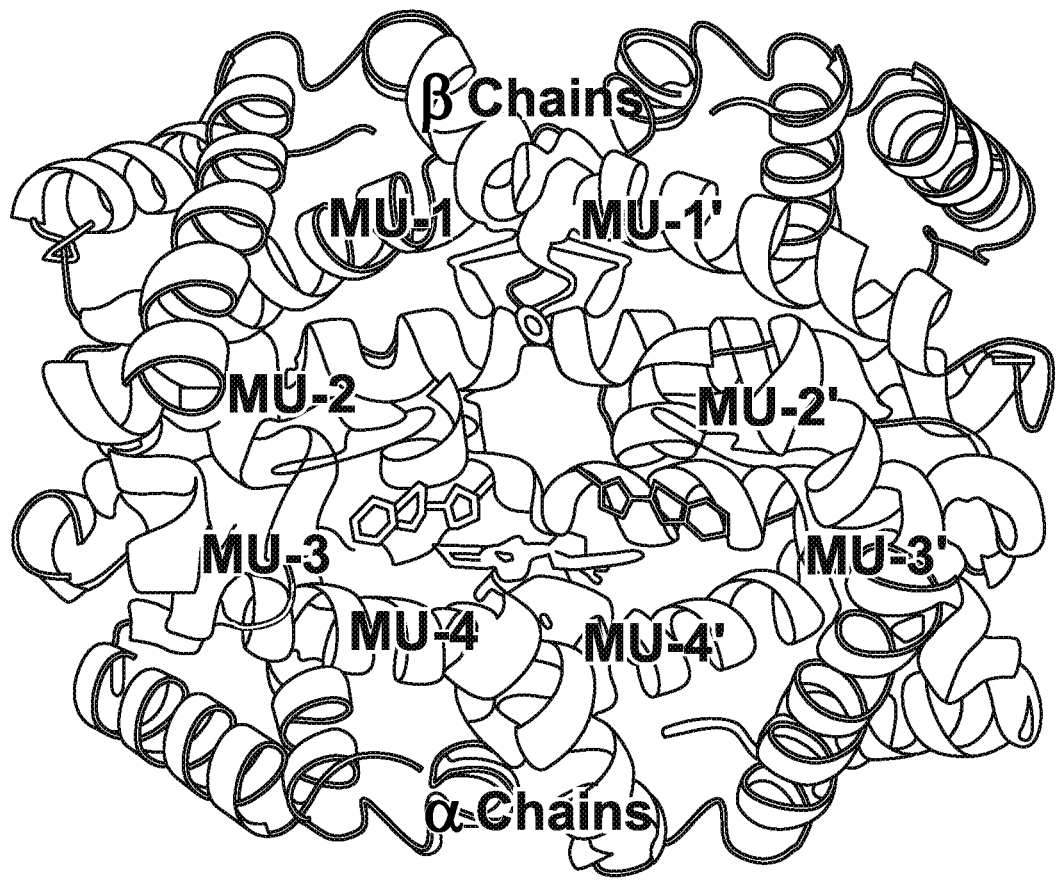
Monomeric unit (MU) of Compound 1
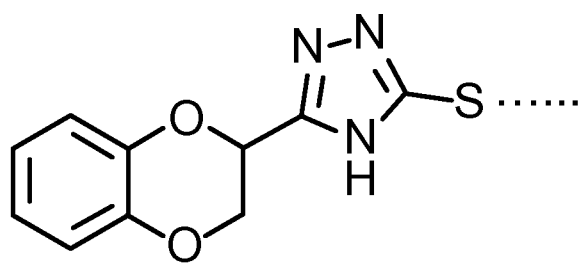
FIG. 9A

HETEROARYL DISULFIDE COMPOUNDS AS ALLOSTERIC EFFECTORS FOR INCREASING THE OXYGEN-BINDING AFFINITY OF HEMOGLOBIN

CLAIM OF PRIORITY

This application is a § 371 National Stage Application of PCT/US2015/011118, filed Jan. 13, 2015, which claims the benefit of priority of U.S. Provisional App. No. 61/926,608, filed Jan. 13, 2014, each of which is incorporated herein by reference in its entirety.

TECHNICAL FIELD

This invention relates to heteroaryl disulfide compounds, which are allosteric effectors that increase the oxygen-being affinity of hemoglobin, which are useful in the treatment of sickle cell disease, high altitude tissue hypoxia, and other conditions.

BACKGROUND

Hemoglobin is a vital iron-containing metalloprotein contained in red blood cells (RBCs). Hemoglobin transports oxygen from the lungs where it loads oxygen from alveolar gas to the tissues where it unloads oxygen. Allosteric effectors are small natural and synthetic molecules that bind to hemoglobin and shift the equilibrium between the oxygenated (R-state) and deoxygenated (T-state) states of hemoglobin by stabilizing the tertiary and quaternary conformations of hemoglobin. Shifting the equilibrium towards the R-state results in increased oxygen-binding affinity of hemoglobin and an increase of oxygenated hemoglobin within the red cell.

Aromatic aldehydes, isothiocyanates, aspirin derivatives, disulfides, and maleimides have been studied as allosteric effectors increasing the oxygen-binding affinity of hemoglobin. These molecules bind to hemoglobin, preferentially stabilizing the R-state, and shifting the allosteric equilibrium towards the R-state which has higher oxygen-binding affinity.

Allosteric effectors that increase the oxygen-binding affinity of hemoglobin may be used to treat sickle cell disease (SCD). SCD is an inherited disorder in which an abnormally mutated hemoglobin (HbS) causes red blood cells to sickle, thereby occluding small blood vessels. Sickled red blood cells can become leaky releasing toxic hemoglobin into the plasma. Sickled red blood cells are cleared from the circulation more rapidly than normal red blood cells leading to anemia. Under hypoxic conditions, deoxygenated HbS tetramers polymerize and distort the RBC into a sickled shape, causing occlusion and thrombosis of small blood vessels, thereby causing ischemia. Increasing the oxygen-binding affinity of sickle RBCs represents a therapeutic strategy for SCD because this increase of oxygen affinity can prevent release of oxygen and decreases the concentration of deoxygenated HbS that can polymerize causing sickling. Other uses of allosteric effectors which increase the oxygen affinity of hemoglobin is the prevention of high altitude tissue hypoxia. Increasing oxygen loading at the lung in extremely hypoxic high altitude exposures can increase survival and prevent systemic hypoxia (Eaton, J. W., Skelton, T. D. & Berger, E., "Survival at extreme altitude: protective effect of increased hemoglobin-oxygen affinity," *Science* 183, 743-4 (1974)). This application addresses these needs and others.

SUMMARY

The present application provides a method of increasing oxygen binding affinity of hemoglobin in red blood cells, comprising contacting said red blood cells with a compound of Formula I:

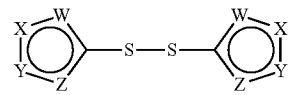

or a pharmaceutically acceptable salt thereof, wherein W, X, Y, and Z are described infra.

In further embodiments, the present application provides a method of improving tolerance to a low oxygen environment or treating a sickle cell disease and complications resulting from sickle cell disease in an individual in need thereof, comprising contacting red blood cells of said individual with a compound of Formula I, or a pharmaceutically acceptable salt thereof.

In other embodiments, the present application provides a method of improving tolerance to a low oxygen environment in an individual in need thereof, comprising contacting red blood cells of said individual with a compound of Formula I, or a pharmaceutically acceptable salt thereof.

In some embodiments, the present application provides a composition comprising red blood cells which have been treated with a compound of Formula I, or a pharmaceutically acceptable salt thereof.

In some embodiments, the present application provides a compound of Formula I, or a pharmaceutically acceptable salt thereof, for use in any of the methods described herein.

In some embodiments, the present application provides use of a compound of Formula I, or a pharmaceutically acceptable salt thereof, for the preparation of a medicament for use in any of the methods described herein.

DESCRIPTION OF DRAWINGS

The file of this patent contains at least one drawing executed in color. Copies of this patent with color drawings will be provided by the Patent and Trademark Office upon request and payment of the necessary fee.

FIG. 7A shows the morphology of sickle red blood cells (Hematocrit ~20%) incubated under normoxic conditions revealed primarily discocytes with some irreversibly sickled cells.

FIG. 7B shows morphology of sickle red blood cells incubated under 4% oxygen at 37° C. for 3 hours revealing sickling of red blood cells.

FIG. 7C-E shows the morphology of sickle red blood cells after sickle red blood cells were mixed with 0.5 mM (c), 1.5 mM (d), and 2 mM (e) of Compound 1 before incubation under 4% oxygen at 37° C. for three hours.

FIG. 7F depicts that treatment with Compound 1 reduced red blood cells sickling induced by hypoxia in a dose-dependent manner.

FIG. 7G depicts oxygen-dissociation curves of the hemolysates at 25° C. ($P_{50}$ measurements of hemolysates from sickled red blood cells treated without or with 0.5, 1.5, and 2.0 mM of Compound 1 were 14, 13, 8, and 4 Torr, respectively).

FIG. 9A depicts the structure of hemoglobin with TD-1 as monomeric units (MUs). α-chains of hemoglobin are blue and β-chains are yellow; the eight MUs are represented by red sticks.

Like reference symbols in the various drawings indicate like elements.

DETAILED DESCRIPTION

Figure 1:
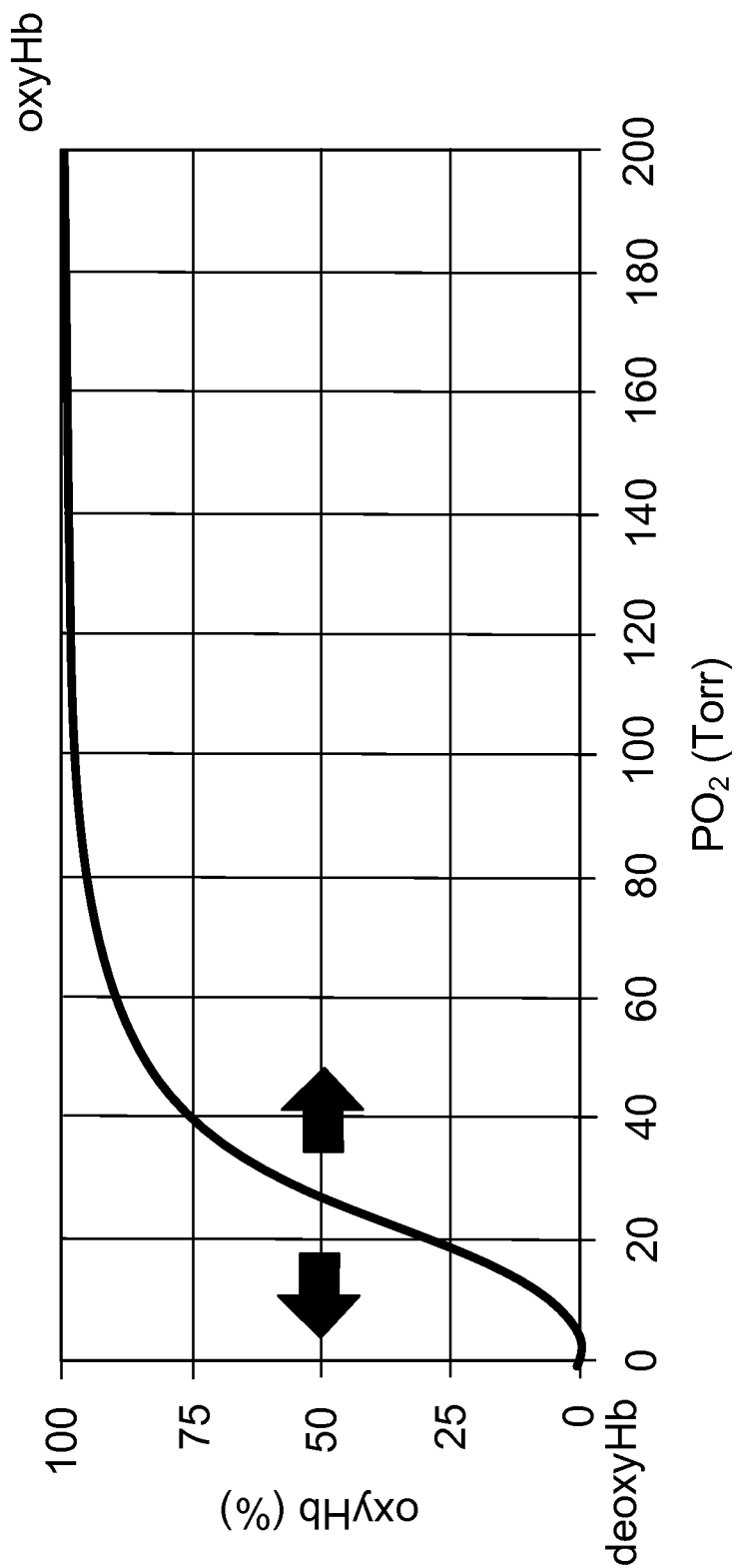
FIG. 1 shows an oxygen dissociation curve (ODC) shifted by an allosteric effector by binding to hemoglobin (Hb). Right shift of ODC (blue arrow)=decrease of the oxygen binding affinity=increase of $P_{50}$ (a partial oxygen pressure at which 50% of hemoglobin is oxygenated in total hemoglobin). Left shift of ODC (red arrow)=increase of the oxygen binding affinity=decrease of $P_{50}$.

The present application provides, inter alia, compounds that are allosteric effectors bind to hemoglobin and shift the equilibrium between the oxygenated (R-state) and deoxygenated (T-state) states of hemoglobin towards the R-state, resulting in increased oxygen-binding affinity of hemoglobin and an increase of oxygenated hemoglobin within red blood cells. Such compounds are useful for treating sickle cell disease and complications resulting there from, as well as improving tolerance to low oxygen environments, which can result from explosive decompression (e.g., plane decompression) or high altitudes, leading to hypoxia.

Accordingly, in some embodiments, the present application provides a compound of Formula I:

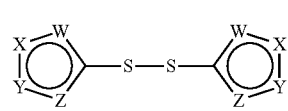

or a pharmaceutically acceptable salt thereof, wherein:
each W is independently selected from $CR^1$ and N;
each X is independently selected from $CR^2$ and N;
each Y is independently selected from $CR^3$, $NR^5$, N, S, and O;
each Z is independently selected from $CR^4$, $NR^6$, N, S, and O;
provided each

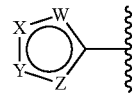

is, independently, a 5-membered heteroaryl ring, which does not contain any S—S, O—O, or S—O bonds; and provided that the selections for W, X, Y, and Z maintain proper valency;

each $R^1$, $R^2$, $R^3$, and $R^4$ are independently selected from H, —($C_{1-4}$ alkylene)-Cy, Cy, $C_{1-6}$ alkyl, $C_{2-6}$ alkenyl, $C_{2-6}$ alkynyl, $C_{1-6}$ haloalkyl, halo, CN, $NO_2$, $OR^a$, $SR^a$, C(=O)$R^a$, C(=O)$NR^cR^d$, C(=O)$OR^a$, OC(=O)$R^b$, OC(=O)$NR^cR^d$, C(=$NR^e$)$NR^cR^d$, $NR^cC$(=$NR^e$)$NR^cR^d$, $NR^cR^d$, $NR^cC$(=O)$R^b$, $NR^cC$(=O)$OR^a$, $NR^cC$(=O)$NR^cR^d$, $NR^cS$(=O)$R^b$, $NR^cS$(=O)$_2R^b$, $NR^cS$(=O)$_2NR^cR^d$, S(=O)$R^b$, S(=O)$NR^cR^d$, S(=O)$_2R^b$, S(=O)$_2NR^cR^d$, and C=$NR^f$; wherein $C_{1-6}$ alkyl, $C_{2-6}$ alkenyl, $C_{2-6}$ alkynyl, and $C_{1-6}$ haloalkyl are each optionally substituted by 1, 2, or 3 independently selected $R^x$ groups;

each $R^5$ and $R^6$ are independently selected from H, —($C_{1-4}$ alkylene)-Cy, Cy, $C_{1-6}$ alkyl, $C_{2-6}$ alkenyl, $C_{2-6}$ alkynyl, $C_{1-6}$ haloalkyl, C(=O)$R^a$, C(=O)$NR^cR^d$, C(=O)$OR^a$, C(=$NR^e$)$NR^cR^d$, S(=O)$R^b$, S(=O)$NR^cR^d$, S(=O)$_2R^b$, and S(=O)$_2NR^cR^d$; wherein $C_{1-6}$ alkyl, $C_{2-6}$ alkenyl, $C_{2-6}$ alkynyl, and $C_{1-6}$ haloalkyl are each optionally substituted by 1, 2, or 3 independently selected $R^x$ groups;

each Cy is independently selected from $C_{3-10}$ monocyclic or bicyclic cycloalkyl, 4-10 membered heterocycloalkyl, phenyl, naphthyl, and 5-10 membered heteroaryl, each of which is optionally substituted by 1, 2, 3, or 4 independently selected $R^x$ groups;

each $R^a$, $R^c$, and $R^d$ are independently selected from H, $C_{1-6}$ alkyl, $C_{2-6}$ alkenyl, $C_{2-6}$ alkynyl, $C_{1-6}$ haloalkyl, and Cy; wherein said $C_{1-6}$ alkyl, $C_{2-6}$ alkenyl, $C_{2-6}$ alkynyl, and $C_{1-6}$ haloalkyl are each optionally substituted with 1, 2, or 3 independently selected $R^x$ groups;

each $R^b$ is independently selected from $C_{1-6}$ alkyl, $C_{2-6}$ alkenyl, $C_{2-6}$ alkynyl, $C_{1-6}$ haloalkyl, and Cy; wherein said $C_{1-6}$ alkyl, $C_{2-6}$ alkenyl, $C_{2-6}$ alkynyl, and $C_{1-6}$ haloalkyl are each optionally substituted with 1, 2, or 3 independently selected $R^x$ groups;

each $R^e$ is independently selected from H, CN, OH, $C_{1-4}$ alkyl, $C_{1-4}$ alkoxy, $NO_2$, $C(O)(C_{1-4}$ alkyl), and $S(=O)_2(C_{1-4}$ alkyl);

each $R^f$ is independently selected from $C_{1-6}$ alkyl, $C_{1-6}$ haloalkyl, and Cy; wherein said $C_{1-6}$ alkyl and $C_{1-6}$ haloalkyl are each optionally substituted with 1, 2, or 3 independently selected $R^x$ groups;

each $R^x$ is independently selected from halo, OH, $NO_2$, CN, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonyloxy, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, the present application provides a method of increasing oxygen binding affinity of hemoglobin in red blood cells, comprising contacting said red blood cells with a compound of Formula I, or a pharmaceutically acceptable salt thereof.

In other embodiments, the present application provides a method of improving tolerance to a low oxygen environment or treating a sickle cell disease and complications resulting from sickle cell disease in an individual in need thereof, comprising contacting red blood cells of said individual with a compound of Formula I, or a pharmaceutically acceptable salt thereof.

In some embodiments, the method is a method of improving tolerance to a low oxygen environment in an individual in need thereof. In some embodiments, the low oxygen environment results from high altitude. In some embodiments, the low oxygen environment results from explosive decompression.

In some embodiments, the method is a method of treating a sickle cell disease or complication resulting from sickle cell disease in an individual in need thereof.

In some embodiments, the contacting can be performed in vivo (i.e., through administration of the compound to an individual in need thereof) or ex vivo. In some embodiments, the compound or salt is administered to the individual in need thereof. In some embodiments, the administering is oral, intravenous, transcutaneous, sublingual, or intrathecal administration. In some embodiments, the administering is intravenous administration. In the case of exposure to a low oxygen environment (e.g., high altitude), the individual may be administered the compound or salt prior to exposure to high altitude in order to avoid the development of high altitude hypoxia. In some embodiments, the compound or salt enables loading of more oxygen on hemoglobin during passage through the lung enabling greater delivery to tissues.

In some embodiments, the contacting comprises contacting said red blood cells of said patient with said compound or salt ex vivo and transfusing the treated red blood cells back to said individual.

In other embodiments, the contacting is performed in combination with an additional therapeutic agent. The additional therapeutic agent may be administered to the individual sequentially or simultaneously. In some embodiments, the additional therapeutic agent is a therapeutic agent for the treatment of SCD or a complication resulting therefrom. In some embodiments, the additional therapeutic agent is hydroxyurea, 5-hydroxymethyl-2-furaldehyde, N-ethylmaleimide, nitric oxide, vorinostat, senicapoc, HQK-1001, erythropoietin, riboflavin, an iron chelator, isobutyramide, zinc, piracetam, etilefrine, L-glutamine, cromolyn sodium, or N-acetylcysteine. In some embodiment, the contacting is performed in combination with a bone marrow transplant.

In some embodiments, the sickle cell disease is selected from sickle cell trait (HbAS), sickle cell anemia (HbSS), sickle cell-hemoglobin C disease (HbSC), sickle cell-hemoglobin E disease, and hemoglobin S-beta-thalassemia. In some embodiments, the sickle cell disease is selected from sickle cell anemia (HbSS), sickle cell-hemoglobin C disease (HbSC), sickle cell-hemoglobin E disease, and hemoglobin S-beta-thalassemia.

In some embodiments, the complication resulting from sickle cell disease is sickle cell crisis. In some embodiments, the sickle cell crisis is selected from vasoocclusive crisis, splenic sequestration crisis, aplastic crisis, hemolytic crisis, and acute chest crisis. In some embodiments, the complication resulting from sickle cell disease is selected from acute painful episodes, dactylitis, infection, overwhelming post-(auto)splenectomy infection (OPSI), anemia, acute chest syndrome, splenic sequestration, stroke, silent stroke, jaundice, infections, leg ulcers. bone damage, pulmonary hypertension, eye damage, organ failure, priapism, joint pain, cholelithiasis (gallstones), cholecystitis, avascular necrosis, osteomyelitis, acute papillary necrosis, background retinopathy, proliferative retinopathy, vitreous hemorrhages, retinal detachments, chronic renal failure, sickle cell nephropathy, neurocognitive decline, intracranial and intracerebral hemorrhage, transient ischemic attacks, infarctive stroke, spinal cord infarction or compression, vestibular dysfunction, sensory hearing loss, growth retardation, delayed puberty, splenic infarction, osteoporosis, bone marrow infarction and necrosis, bone marrow infarction with resulting exacerbation of anemia or pancytopenia, fat embolism, orbital compression syndrome, myocardial infarction, acute heptatic dysfunction, and pregnancy complications of mother or fetus.

Other complications resulting from SCD include, but are not limited to, those in Vinchinsky, "Overview of the clinical manifestation of sickle cell disease", UpToDate, 2014, pages 1-25. In some embodiments, the complications resulting from SCD are selected from painful episodes, symptomatic anemia, susceptibility to infection, stroke, cardiopulmonary complications, renal involvement, leg ulcers, recurrent priapism in males, anemia, hyperhemolytic crisis, multiorgan failure, osteomyelitis, reticulocytosis of 3 to 15 percent, acute hepatic ischemia, benign cholestasis, hepatic sequestration crisis, transfusional iron overload, acute and chronic cholelithiasis secondary to pigmented gallstones, acute and chronic liver disease secondary to hepatitis C virus infection (HCV) complicating blood transfusion, retinopathy, proliferative sickle retinopathy, unconjugated hyperbilirubinemia, elevated serum lactate dehydrogenase, and low serum haptoglobin As used herein, the term "contacting" refers to the bringing together of indicated moieties in an ex vivo or in vivo. For example, "contacting" blood or a red blood cell with a compound described herein includes the administration of the compound to an individual or patient, such as a human, as well as, for example, introducing a compound of the invention into a blood composition.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician. In some embodiments, the therapeutically effective amount is about 5 mg to about 1000 mg, or about 10 mg to about 500 mg.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder (i.e., arresting further development of the pathology and/or symptomatology); and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

It is further appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination.

Compounds

In some embodiments, each W is selected from $CR^1$ and N.

In some embodiments, each X is selected from $CR^2$ and N.

In some embodiments, each Y is selected from $CR^3$, $NR^5$, N, and O.

In some embodiments, each Z is selected from $CR^4$, $NR^6$, and S.

In some embodiments, each

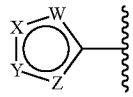

is a moiety of Formula (A):

(A)

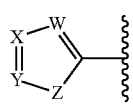

wherein:
each W is independently selected from $CR^1$ and N;
each X is independently selected from $CR^2$ and N;
each Y is independently selected from $CR^3$ and N; and
each Z is independently selected from $NR^6$, S, and O.

In some embodiments, each

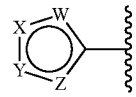

is a moiety of Formula (B):

(B)

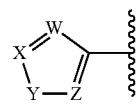

wherein:
each W is independently selected from $CR^1$ and N;
each X is independently selected from $CR^2$ and N;
each Y is independently selected from $NR^5$, S, and O; and
each Z is independently selected from $CR^4$ and N.

In some embodiments, each

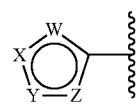

is selected from the following moieties:

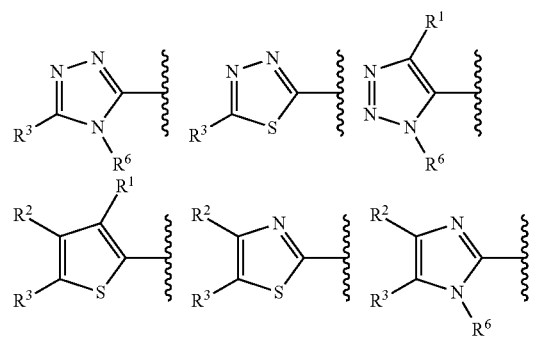

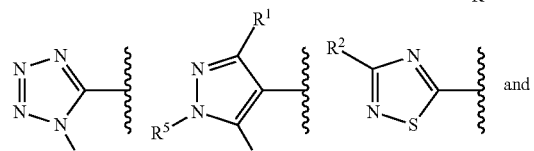

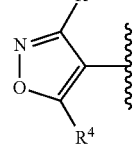

In some embodiments, each

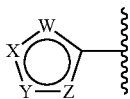

is identical.

In some embodiments, each $R^1$ is independently selected from H, $C_{1-6}$ alkyl, $C_{1-6}$ haloalkyl, halo, CN, $OR^a$, $SR^a$, $C(=O)R^a$, $C(=O)NR^cR^d$, $C(=O)OR^a$, $NR^cR^d$, $NR^cC(=O)R^b$, $NR^cC(=O)OR^a$, $NR^cC(=O)NR^cR^d$, $NR^cS(=O)_2R^b$, $S(=O)_2R^b$, and $S(=O)_2NR^cR^d$. In some embodiments, each $R^1$ is independently selected from H, $C_{1-6}$ alkyl, and $C_{1-6}$ alkoxycarbonyl.

In some embodiments, each $R^2$ is independently selected from H, $C_{1-6}$ alkyl, $C_{1-6}$ haloalkyl, halo, and CN. In some embodiments, each $R^2$ is independently selected from H, halo, and $C_{1-6}$ alkyl.

In some embodiments, each $R^3$ is independently selected from H, Cy, $C_{1-6}$ alkyl, $C_{1-6}$ haloalkyl, halo, CN, $OR^a$, $SR^a$, $C(=O)R^a$, $C(=O)NR^cR^d$, $C(=O)OR^a$, $NR^cR^d$, $NR^cC(=O)R^b$, $NR^cC(=O)OR^a$, $NR^cC(=O)NR^cR^d$, $NR^cS(=O)_2R^b$, $S(=O)_2R^b$, $S(=O)_2NR^cR^d$, and $C=NR^f$. In some embodiments, each $R^3$ is independently selected from H, Cy, $OR^a$, $SR^a$, $C(=O)R^a$, $C(=O)OR^a$, $NR^cR^d$, and $C=NR^f$.

In some embodiments, each $R^5$ is independently selected from H, $C_{1-6}$ alkyl, $C_{1-6}$ haloalkyl, and Cy. In some embodiments, each $R^5$ is independently selected from H and Cy.

In some embodiments, each $R^4$ is independently selected from H, $C_{1-6}$ alkyl, $C_{1-6}$ haloalkyl, halo, CN, $OR^a$, $SR^a$, $C(=O)R^a$, $C(=O)NR^cR^d$, $C(=O)OR^a$, $NR^cR^d$, $NR^cC(=O)R^b$, $NR^cC(=O)OR^a$, $NR^cC(=O)NR^cR^d$, $NR^cS(=O)_2R^b$, $S(=O)_2R^b$, and $S(=O)_2NR^cR^d$. In some embodiments, each $R^4$ is independently selected from H, $C_{1-6}$ alkyl, and $C(=O)R^a$.

In some embodiments, each $R^6$ is independently selected from H, $C_{1-6}$ alkyl, $C_{1-6}$ haloalkyl, and Cy. In some embodiments, each $R^6$ is independently selected from H and Cy.

In some embodiments, each Cy is independently selected from $C_{3-7}$ monocyclic cycloalkyl, 4-10 membered heterocycloalkyl, phenyl, and 5-10 membered heteroaryl, each of which is optionally substituted by 1, 2, 3, or 4 independently selected $R^x$ groups. In some embodiments, each Cy is 4-10 membered heterocycloalkyl, which is optionally substituted by 1, 2, 3, or 4 independently selected $R^x$ groups. In some embodiments, each Cy is phenyl, which is optionally substituted by 1, 2, 3, or 4 independently selected $R^x$ groups. In some embodiments, each Cy is 5-10 membered heteroaryl, which is optionally substituted by 1, 2, 3, or 4 independently selected $R^x$ groups. In some embodiments, each Cy is independently selected from phenyl, a pyridine ring, and a benzo[b][1,4]dioxane ring, each of which is optionally substituted by 1, 2, 3, or 4 independently selected $R^x$ groups.

In some embodiments, each $R^a$, $R^c$, and $R^d$ are independently selected from H, $C_{1-6}$ alkyl, and $C_{1-6}$ haloalkyl; each $R^b$ is independently selected from $C_{1-6}$ alkyl and $C_{1-6}$ haloalkyl; and each $R^f$ is independently selected from $C_{1-6}$ alkyl, $C_{1-6}$ haloalkyl, and Cy.

In some embodiments, each

is a moiety of Formula (A) or (B):

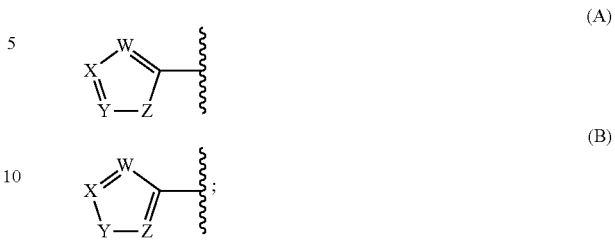

wherein:

each $R^1$ is independently selected from H, $C_{1-6}$ alkyl, $C_{1-6}$ haloalkyl, halo, CN, $OR^a$, $SR^a$, $C(=O)R^a$, $C(=O)NR^cR^d$, $C(=O)OR^a$, $NR^cR^d$, $NR^cC(=O)R^b$, $NR^cC(=O)OR^a$, $NR^cC(=O)NR^cR^d$, $NR^cS(=O)_2R^b$, $S(=O)_2R^b$, and $S(=O)_2NR^cR^d$;

each $R^2$ is independently selected from H, $C_{1-6}$ alkyl, $C_{1-6}$ haloalkyl, halo, and CN;

each $R^3$ is independently selected from H, Cy, $C_{1-6}$ alkyl, $C_{1-6}$ haloalkyl, halo, CN, $OR^a$, $SR^a$, $C(=O)R^a$, $C(=O)NR^cR^d$, $C(=O)OR^a$, $NR^cR^d$, $NR^cC(=O)R^b$, $NR^cC(=O)OR^a$, $NR^cC(=O)NR^cR^d$, $NR^cS(=O)_2R^b$, $S(=O)_2R^b$, $S(=O)_2NR^cR^d$, and $C=NR^f$;

each $R^5$ is independently selected from H, $C_{1-6}$ alkyl, $C_{1-6}$ haloalkyl, and Cy;

each $R^4$ is independently selected from H, $C_{1-6}$ alkyl, $C_{1-6}$ haloalkyl, halo, CN, $OR^a$, $SR^a$, $C(=O)R^a$, $C(=O)NR^cR^d$, $C(=O)OR^a$, $NR^cR^d$, $NR^cC(=O)R^b$, $NR^cC(=O)OR^a$, $NR^cC(=O)NR^cR^d$, $NR^cS(=O)_2R^b$, $S(=O)_2R^b$, and $S(=O)_2NR^cR^d$;

each $R^6$ is independently selected from H, $C_{1-6}$ alkyl, $C_{1-6}$ haloalkyl, and Cy;

each Cy is independently selected from $C_{3-7}$ monocyclic cycloalkyl, 4-10 membered heterocycloalkyl, phenyl, and 5-10 membered heteroaryl, each of which is optionally substituted by 1, 2, 3, or 4 independently selected $R^x$ groups;

each $R^a$, $R^c$, and $R^d$ are independently selected from H, $C_{1-6}$ alkyl, and $C_{1-6}$ haloalkyl;

each $R^b$ is independently selected from $C_{1-6}$ alkyl and $C_{1-6}$ haloalkyl; and each $R^f$ is independently selected from $C_{1-6}$ alkyl, $C_{1-6}$ haloalkyl, and Cy;

provided that for Formula (A):

each W is independently selected from $CR^1$ and N;

each X is independently selected from $CR^2$ and N;

each Y is independently selected from $CR^3$ and N; and each Z is independently selected from $NR^6$, S, and O; and and provided that for Formula (B):

each W is independently selected from $CR^1$ and N;

each X is independently selected from $CR^2$ and N;

each Y is independently selected from $NR^5$, S, and O; and each Z is independently selected from $CR^4$ and N.

In some embodiments, each is a moiety of Formula (A) or (B):

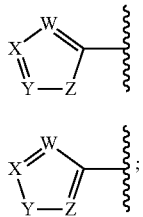

wherein:
each $R^1$ is independently selected from H, $C_{1-6}$ alkyl, and $C_{1-6}$ alkoxycarbonyl;
each $R^2$ is independently selected from H, halo, and $C_{1-6}$ alkyl;
each $R^3$ is independently selected from H, Cy, $OR^a$, $SR^a$, $C(=O)R^a$, $C(=O)OR^a$, $NR^cR^d$, and $C=NR^f$;
each $R^5$ is independently selected from H and Cy;
each $R^4$ is independently selected from H, $C_{1-6}$ alkyl, and $C(=O)R^a$;
each $R^6$ is independently selected from H and Cy;
each Cy is independently selected from $C_{3-7}$ monocyclic cycloalkyl, 4-10 membered heterocycloalkyl, phenyl, and 5-10 membered heteroaryl, each of which is optionally substituted by 1, 2, 3, or 4 independently selected $R^x$ groups;
each $R^a$, $R^c$, and $R^d$ are independently selected from H, $C_{1-6}$ alkyl, and $C_{1-6}$ haloalkyl; each $R^b$ is independently selected from $C_{1-6}$ alkyl and $C_{1-6}$ haloalkyl; and
each $R^f$ is independently selected from $C_{1-6}$ alkyl, $C_{1-6}$ haloalkyl, and Cy;
provided that for Formula (A):
each W is independently selected from $CR^1$ and N;
each X is independently selected from $CR^2$ and N;
each Y is independently selected from $CR^3$ and N; and
each Z is independently selected from $NR^6$, S, and O; and
and provided that for Formula (B):
each W is independently selected from $CR^1$ and N;
each X is independently selected from $CR^2$ and N;
each Y is independently selected from $NR^5$, S, and O; and
each Z is independently selected from $CR^4$ and N.
In some embodiments, the compound is selected from:
1,2-bis(5-(2,3-dihydrobenzo[b][1,4]dioxin-2-yl)-4H-1,2,4-triazol-3-yl)disulfane;
1,2-bis(5-(pyridin-4-yl)-4H-1,2,4-triazol-3-yl)disulfane;
1,2-bis(5-(pyridin-3-yl)-4H-1,2,4-triazol-3-yl)disulfane;
1,2-bis(5-(furan-2-yl)-4H-1,2,4-triazol-3-yl)disulfane;
1,2-di(thiazol-2-yl)disulfane;
5,5'-disulfanediylbis(1,3,4-thiadiazol-2-amine);
2,2'-disulfanediylbis(1H-imidazol-5-ol);
1,2-di(4H-1,2,4-triazol-3-yl)disulfane;
1,2-di(1H-1,2,3-triazol-5-yl)disulfane;
1,2-bis(1-phenyl-1H-tetrazol-5-yl)disulfane;
1,1'-(2,2'-disulfanediylbis(4-methylthiazole-5,2-diyl))diethanone;
(NE,N'E)-5,5'-disulfanediylbis(N-benzylidene-1,3,4-thiadiazol-2-amine);
5,5'-disulfanediylbis(1,3,4-thiadiazole-2-thiol);
1,2-bis(3-chloro-1,2,4-thiadiazol-5-yl)disulfane;
1,2-di(1H-pyrazol-4-yl)disulfane;
4,4'-disulfanediylbis(3-methyl-1-phenyl-1H-pyrazole-5-carbaldehyde);
1,2-bis(3,5-dimethylisoxazol-4-yl)disulfane;
tetraethyl 5,5'-disulfanediylbis(3-methylthiophene-2,4-dicarboxylate); and
5,5'-disulfanediylbis(4H-1,2,4-triazol-3-amine);
or a pharmaceutically acceptable salt thereof.

At various places in the present specification, substituents of compounds described herein are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in the present specification, linking substituents are described. Where the structure clearly requires a linking group, the Markush variables listed for that group are understood to be linking groups. For example, if the structure requires a linking group and the Markush group definition for that variable lists "alkyl" or "aryl" then it is to be understood that the "alkyl" or "aryl" represents a linking alkylene group or arylene group, respectively.

At various places in the present specification, rings are described (e.g., "a triazole ring"). Unless otherwise specified, these rings can be attached to the rest of the molecule at any ring member as permitted by valency. For example, the term "a 2H-tetrahydropyran ring" may refer to a 2H-tetrahydropyran-2-yl, 2H-tetrahydropyran-3-yl, 2H-tetrahydropyran-4-yl ring, etc.

The term "n-membered" where n is an integer typically describes the number of ring-forming atoms in a moiety where the number of ring-forming atoms is n. For example, 2H-tetrahydropyran is an example of a 6-membered heterocycloalkyl ring, 1H-1,2,4-triazole is an example of a 5-membered heteroaryl ring, pyridine is an example of a 6-membered heteroaryl ring, and 1,2,3,4-tetrahydro-naphthalene is an example of a 10-membered cycloalkyl group.

For compounds in which a variable appears more than once, each variable can be a different moiety independently selected from the group defining the variable. For example, where a structure is described having two R groups that are simultaneously present on the same compound, the two R groups can represent different moieties independently selected from the group defined for R. In another example, when an optionally multiple substituent is designated in the form:

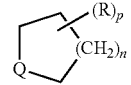

then it is to be understood that substituent R can occur p number of times on the ring, and R can be a different moiety at each occurrence. It is to be understood that each R group may replace any hydrogen atom attached to a ring atom, including one or both of the $(CH_2)_n$ hydrogen atoms. Further, in the above example, should the variable Q be defined to include hydrogens, such as when Q is said to be $CH_2$, NH, etc., any floating substituent such as R in the above example, can replace a hydrogen of the Q variable as well as a hydrogen in any other non-variable component of the ring.

As used herein, the phrase "optionally substituted" means unsubstituted or substituted. As used herein, the term "substituted" means that a hydrogen atom is removed and replaced by a substituent. It is to be understood that substitution at a given atom is limited by valency.

As used herein, the term "$C_{n-m}$ alkyl", employed alone or in combination with other terms, refers to a saturated hydrocarbon group that may be straight-chain or branched, having n to m carbon atoms. In some embodiments, the alkyl group contains 1 to 6, 1 to 4 or 1 to 3 carbon atoms. Examples of alkyl moieties include, but are not limited to, chemical groups such as methyl, ethyl, n-propyl, isopropyl, n-butyl, isobutyl, sec-butyl, tert-butyl, n-pentyl, 2-methyl-1-butyl, 3-pentyl, n-hexyl, 1,2,2-trimethylpropyl, and the like.

As used herein, the term "alkylene", employed alone or in combination with other terms, refers to a divalent alkyl linking group, which can be branched or straight-chain, where the two substituents may be attached any position of the alkylene linking group. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl, and the like.

As used herein, "$C_{n-m}$ alkenyl" refers to an alkyl group having one or more double carbon-carbon bonds and having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl, and the like.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkoxy", employed alone or in combination with other terms, refers to a group of formula —O-alkyl, wherein the alkyl group has n to m carbons. In some embodiments, the alkyl group contains 1 to 6, 1 to 4 or 1 to 3 carbon atoms. Example alkoxy groups include methoxy, ethoxy, and propoxy (e.g., n-propoxy and isopropoxy).

As used herein, the term "amino" refers to a group of formula —$NH_2$.

As used herein, the term "$C_{n-m}$ alkylamino" refers to a group of formula —NH(alkyl), wherein the alkyl group n-m carbon atoms. In some embodiments, the alkyl group contains 1 to 6, 1 to 4 or 1 to 3 carbon atoms.

As used herein, the term "di($C_{n-m}$ alkyl)amino" refers to a group of formula —N(alkyl)$_2$, wherein the two alkyl groups each has, independently, n to m carbon atoms. In some embodiments, each alkyl group independently has 1 to 6, 1 to 4 or 1 to 3 carbon atoms.

As used herein, the term "$C_{n-m}$ alkoxycarbonyl" refers to a group of formula —C(O)O-alkyl, wherein the alkyl group has n to m carbon atoms. In some embodiments, the alkyl group contains 1 to 6, 1 to 4 or 1 to 3 carbon atoms.

As used herein, the term "$C_{n-m}$ alkylcarbonyl" refers to a group of formula —C(O)— alkyl, wherein the alkyl group has n to m carbon atoms. In some embodiments, the alkyl group contains 1 to 6, 1 to 4 or 1 to 3 carbon atoms.

As used herein, the term "carboxy" refers to a group of formula —C(O)OH.

As used herein, the term "thio" refers to a group of formula —SH.

As used herein, the term "$C_{n-m}$ alkylthio" refers to a group of formula —S-(alkyl), wherein the alkyl group has n to m carbon atoms. In some embodiments, the alkyl group contains 1 to 6, 1 to 4 or 1 to 3 carbon atoms.

As used herein, the term "$C_{n-m}$ alkylsulfinyl" refers to a group of formula —S(O)— alkyl, wherein the alkyl group has n to m carbon atoms. In some embodiments, the alkyl group contains 1 to 6, 1 to 4 or 1 to 3 carbon atoms.

As used herein, the term "$C_{n-m}$ alkylsulfonyl" refers to a group of formula —S(O)$_2$—alkyl, wherein the alkyl group has n to m carbon atoms. In some embodiments, the alkyl group contains 1 to 6, 1 to 4 or 1 to 3 carbon atoms.

As used herein, the term "$C_{n-m}$ alkylcarbonyloxy" refers to a group of formula —OC(O)-alkyl, wherein the alkyl group has n to m carbon atoms. In some embodiments, the alkyl group contains 1 to 6, 1 to 4 or 1 to 3 carbon atoms.

As used herein, the term "$C_{n-m}$ alkylcarbonylamino" refers to a group of formula —NHC(O)-alkyl, wherein the alkyl group has n to m carbon atoms. In some embodiments, the alkyl group contains 1 to 6, 1 to 4 or 1 to 3 carbon atoms.

As used herein, the term "aminocarbonylamino" refers to a group of formula —NHC(O)$NH_2$.

As used herein, the term "$C_{n-m}$ alkylaminocarbonylamino," refers to a group of formula —NHC(O)NH(alkyl), wherein said alkyl has n to m carbon atoms. In some embodiments, the alkyl group contains 1 to 6, 1 to 4 or 1 to 3 carbon atoms. In some embodiments, each alkyl group independently has 1 to 6, 1 to 4 or 1 to 3 carbon atoms.

As used herein, the term "di($C_{n-m}$ alkylaminocarbonylamino" refers to a group of formula —NHC(O)N(alkyl)$_2$, wherein each alkyl independently has n to m carbon atoms. In some embodiments, each alkyl group independently has 1 to 6, 1 to 4 or 1 to 3 carbon atoms.

As used herein, the term "carbamyl" refers to a group of formula —C(O)—$NH_2$.

As used herein, the term "$C_{n-m}$ alkylcarbamyl" refers to a group of formula —C(O)—NH(alkyl), wherein the alkyl group has n to m carbon atoms. In some embodiments, the alkyl group contains 1 to 6, 1 to 4 or 1 to 3 carbon atoms.

As used herein, the term "di($C_{n-m}$-alkyl)carbamyl" refers to a group of formula C(O)N(alkyl)$_2$, wherein the two alkyl groups each has, independently, n to m carbon atoms. In some embodiments, each alkyl group independently has 1 to 6, 1 to 4 or 1 to 3 carbon atoms.

As used herein, the term "$C_{n-m}$ alkylsulfonylamino" refers to a group of formula —NHS(O)$_2$-alkyl, wherein said alkyl has n to m carbon atoms. In some embodiments, the alkyl group contains 1 to 6, 1 to 4 or 1 to 3 carbon atoms.

As used herein, the term "aminosulfonyl" refers to a group of formula —S(O)$_2NH_2$.

As used herein, the term "$C_{n-m}$ alkylaminosulfonyl" refers to a group of formula —S(O)$_2$NH(alkyl), wherein said alkyl has n to m carbon atoms. In some embodiments, the alkyl group contains 1 to 6, 1 to 4 or 1 to 3 carbon atoms.

As used herein, the term "di($C_{n-m}$ alkyl)aminosulfonyl" refers to a group of formula —S(O)$_2$N(alkyl)$_2$, wherein each alkyl independently has n to m carbon atoms. In some embodiments, each alkyl group independently has 1 to 6, 1 to 4 or 1 to 3 carbon atoms.

As used herein, the term "aminosulfonylamino" refers to a group of formula —NHS(O)$_2NH_2$.

As used herein, the term "$C_{n-m}$ alkylaminosulfonylamino," refers to a group of formula —NHS(O)$_2$NH(alkyl), wherein said alkyl has n to m carbon atoms. In some embodiments, the alkyl group contains 1 to 6, 1 to 4 or 1 to 3 carbon atoms.

As used herein, the term "di($C_{n-m}$ alkylaminosulfonylamino" refers to a group of formula —NHS(O)$_2$N(alkyl)$_2$, wherein each alkyl independently has n to m carbon atoms. In some embodiments, each alkyl group independently has 1 to 6, 1 to 4 or 1 to 3 carbon atoms.

As used herein, the term "HO—$C_{n-m}$-alkyl" refers to a group of formula -alkylene-OH, wherein said alkylene group has n to m carbon atoms. In some embodiments, the alkylene group has 1 to 3 carbon atoms.

As used herein, the term "$C_{o-p}$ alkoxy-$C_{n-m}$-alkyl" refers to a group of formula -alkylene-O-alkyl, wherein said alkylene group has n to m carbon atoms and said alkyl group has o to p carbon atoms. In some embodiments, the alkyl and alkylene groups each independently have 1 to 3 carbon atoms.

As used herein, the term "carbonyl", employed alone or in combination with other terms, refers to a —C(O)— group.

As used herein, "halo" or "halogen", employed alone or in combination with other terms, includes fluoro, chloro, bromo, and iodo.

As used herein, the term "$C_{n-m}$ haloalkyl", employed alone or in combination with other terms, refers to an $C_{n-m}$ alkyl group having up to {2(n to m)+1} halogen atoms which may either be the same or different. In some embodiments, the halogen atoms are fluoro atoms. In some embodiments, the alkyl group has 1 to 6 or 1 to 4 carbon atoms. Example haloalkyl groups include $CF_3$, $C_2F_5$, $CHF_2$, $CCl_3$, $CHCl_2$, $C_2Cl_5$, and the like. In some embodiments, the haloalkyl group is a fluoroalkyl group.

As used herein, "$C_{n-m}$ haloalkoxy" refers to a group of formula —O-haloalkyl having n to m carbon atoms. An example haloalkoxy group is $OCF_3$. In some embodiments, the haloalkoxy group is fluorinated only. In some embodiments, the alkyl group has 1 to 6 or 1 to 4 carbon atoms.

As used herein, the term "cyano-$C_{n-m}$ alkyl" refers to a $C_{n-m}$ alkyl substituted by a cyano group. In some embodiments, the alkyl group has 1 to 3 carbon atoms.

As used herein, the appearance of the term "monocyclic" before the name of a moiety indicates that the moiety has a single ring.

As used herein, the term "cycloalkyl", employed alone or in combination with other terms, refers to a non-aromatic cyclic hydrocarbon moiety, which may optionally contain one or more alkenylene groups as part of the ring structure. Cycloalkyl groups can include mono- or polycyclic (e.g., having 2, 3 or 4 fused, spirocyclic, or bridged rings) ring systems. Also included in the definition of cycloalkyl are moieties that have one or more aromatic rings fused (i.e., having a bond in common with) to the cycloalkyl ring, for example, benzo derivatives of cyclopentane, cyclopentene, cyclohexane, and the like. One or more ring-forming carbon atoms of a cycloalkyl group can be oxidized to form carbonyl linkages. In some embodiments, cycloalkyl is a 3-10 membered cycloalkyl, which is monocyclic or bicyclic. In some embodiments, cycloalkyl is a 3-6 or 3-7 monocyclic cycloalkyl. Exemplary cycloalkyl groups include 1,2,3,4-tetrahydro-naphthalene, cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. In some embodiments, the cycloalkyl group is cyclopropyl, cyclobutyl, cyclopentyl, or cyclohexyl.

As used herein, the term "aryl", employed alone or in combination with other terms, refers to a monocyclic or polycyclic (e.g., having 2, 3 or 4 fused rings) aromatic hydrocarbon, such as, but not limited to, phenyl, 1-naphthyl, 2-naphthyl, anthracenyl, phenanthrenyl, and the like. In some embodiments, aryl is $C_{6-10}$ aryl. In some embodiments, the aryl group is a naphthalene ring or phenyl ring. In some embodiments, the aryl group is phenyl.

As used herein, the term "heteroaryl", employed alone or in combination with other terms, refers to a monocyclic or polycyclic (e.g., having 2, 3 or 4 fused rings) aromatic hydrocarbon moiety, having one or more heteroatom ring members selected from nitrogen, sulfur and oxygen. In some embodiments, heteroaryl is a 5-10 membered heteroaryl, which is monocyclic or bicyclic, comprising 1 to 9 carbon atoms and 1, 2, 3, or 4 heteroatom ring members independently selected from nitrogen, sulfur and oxygen. In some embodiments, heteroaryl is a 5-6 membered heteroaryl, which is monocyclic or bicyclic, comprising 1 to 5 carbon atoms and 1, 2, 3, or 4 heteroatom ring members independently selected from nitrogen, sulfur, and oxygen. When the heteroaryl group contains more than one heteroatom ring member, the heteroatoms may be the same or different. Example heteroaryl groups include, but are not limited to, pyridine, pyrimidine, pyrazine, pyridazine, pyrrole, pyrazole, azolyl, oxazole, thiazole, imidazole, furan, thiophene, quinoline, isoquinoline, indole, benzothiophene, benzofuran, benzisoxazole, imidazo[1,2-b]thiazole, purine, or the like.

A five-membered ring heteroaryl is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl.

A six-membered ring heteroaryl is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl and pyridazinyl.

As used herein, the term "heteroarylalkyl" refers to a group of formula alkylene-heteroaryl. In some embodiments, heteroarylalkyl is $C_{1-9}$ heteroaryl-$C_{1-3}$ alkyl, wherein the heteroaryl portion is monocyclic or bicyclic and has 1, 2, 3, or 4 heteroatom ring members independently selected from nitrogen, sulfur and oxygen.

As used herein, the term "heterocycloalkyl", employed alone or in combination with other terms, refers to non-aromatic ring system, which may optionally contain one or more alkenylene groups as part of the ring structure, and which has at least one heteroatom ring member independently selected from nitrogen, sulfur and oxygen. When the heterocycloalkyl groups contains more than one heteroatom, the heteroatoms may be the same or different. Heterocycloalkyl groups can include mono- or polycyclic (e.g., having 2, 3 or 4 fused, spirocyclic, or bridged rings) ring systems. Also included in the definition of heterocycloalkyl are moieties that have one or more aromatic rings fused (i.e., having a bond in common with) to the non-aromatic ring, for example, 1,2,3,4-tetrahydro-quinoline, 2,3-dihydrobenzo[b][1,4]dioxane, and the like. The carbon atoms or heteroatoms in the ring(s) of the heterocycloalkyl group can be oxidized to form a carbonyl, or sulfonyl group (or other oxidized linkage) or a nitrogen atom can be quaternized. In some embodiments, heterocycloalkyl is 5-10 membered heterocycloalkyl, which is monocyclic or bicyclic, comprising 2 to 9 carbon atoms and 1, 2, 3, or 4 heteroatom ring members independently selected from nitrogen, sulfur, and oxygen. Examples of heterocycloalkyl groups include 2,3-dihydrobenzo[b][1,4]dioxane, 1,2,3,4-tetrahydro-quinoline, azetidine, azepane, pyrrolidine, piperidine, piperazine, morpholine, thiomorpholine, pyran, and a 2-oxo-1,3-oxazolidine ring.

As used herein, the term "heterocycloalkylalkyl" refers to a group of formula -alkylene-heterocycloalkyl. In some embodiments, heterocycloalkylalkyl is $C_{2-9}$ heterocycloalkyl-$C_{1-3}$ alkyl, wherein the heterocycloalkyl portion is monocyclic or bicyclic and has 1, 2, 3, or 4 heteroatom ring members independently selected from nitrogen, sulfur and oxygen.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

The compounds described herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

The compounds described herein can also include all isotopes of atoms occurring in the intermediates or final compounds. Isotopes include those atoms having the same atomic number but different mass numbers. For example, isotopes of hydrogen include tritium and deuterium.

The term, "compound," as used herein is meant to include all stereoisomers, geometric iosomers, tautomers, and isotopes of the structures depicted.

All compounds, and pharmaceutically acceptable salts thereof, can be found together with other substances such as water and solvents (e.g., hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds described herein, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g. a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety. In some embodiments, the compounds described herein include the N-oxide forms.

Synthesis

The compounds described herein, including salts thereof, can be prepared using organic synthesis techniques and can be synthesized according to any of numerous possible synthetic routes, such as those in the Schemes below. The reactions for preparing compounds described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in Wuts and Greene, Protective Groups in Organic Synthesis, 4th ed., John Wiley & Sons: New Jersey, (2007), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC) or thin layer chromatography (TLC).

Starting materials used in the following schemes can be purchased or prepared by methods described in the chemical literature, or by adaptations thereof, using methods known by those skilled in the art. The order in which the steps are performed can vary depending on the protecting or functional groups introduced and the reagents and reaction conditions used, but would be apparent to those skilled in the art.

The coupling of thiols to form disulfide linkages can be accomplished as outlined in Schemes 1-4. Methods of disulfide synthesis include, but are not limited to thiol dimerization in the presence of concentrated sulfuric acid in acetic acid (Scheme 1), thiol dimerization in the presence of hydrogen peroxide in ethanol (Scheme 2), thiol dimerization in the presence of sulfuric acid in hydrogen peroxide (Scheme 3), and thiol dimerization in aqueous base in the presence of ammonium persulfate, wherein W, X, Y, and Z may be optionally substituted.

Scheme 1

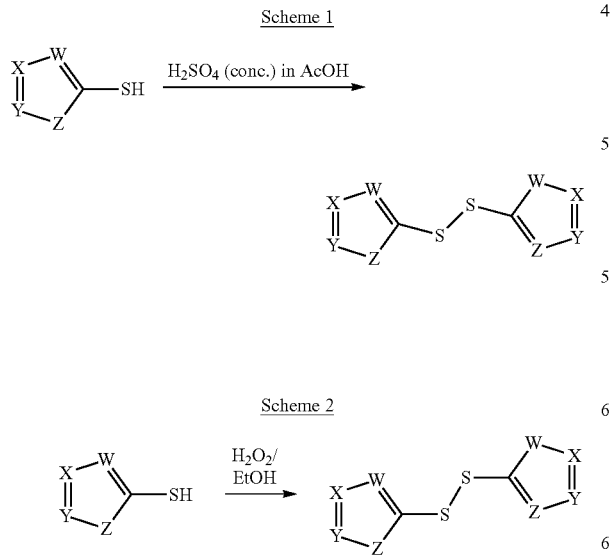

Scheme 3

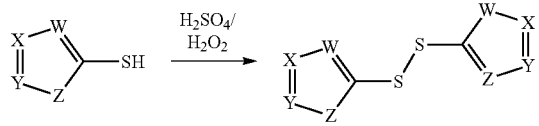

Scheme 4

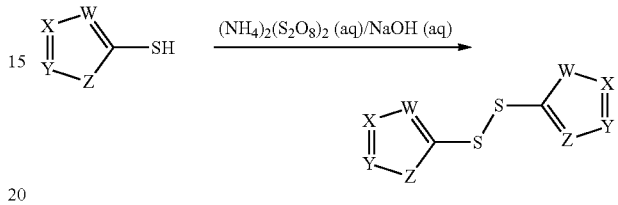

Compound 1 was prepared according to Scheme 5, shown below. The coupling of 2,3-dihydrobenzo[b][1,4]dioxine-2-carboxylic acid and hydrazinecarbothioamide via an addition reaction and subsequent dehydration was performed in the presence of hydroxybenzotriazole (HOBt), 1-ethyl-3-(3-dimethylaminopropyl)carbodiimide, and triethylamine (TEA) dissolved in tetrahydrofuran (THF). A cyclization reaction of 2-(2,3-dihydrobenzo[b][1,4]dioxine-2-carbonyl)hydrazinecarbothioamide was performed in an aqueous solution of NaOH (95%) to afford the thiol intermediate. Finally, the ttle compound was formed by treating the thiol with sulfuric acid in acetic acid.

Scheme 5

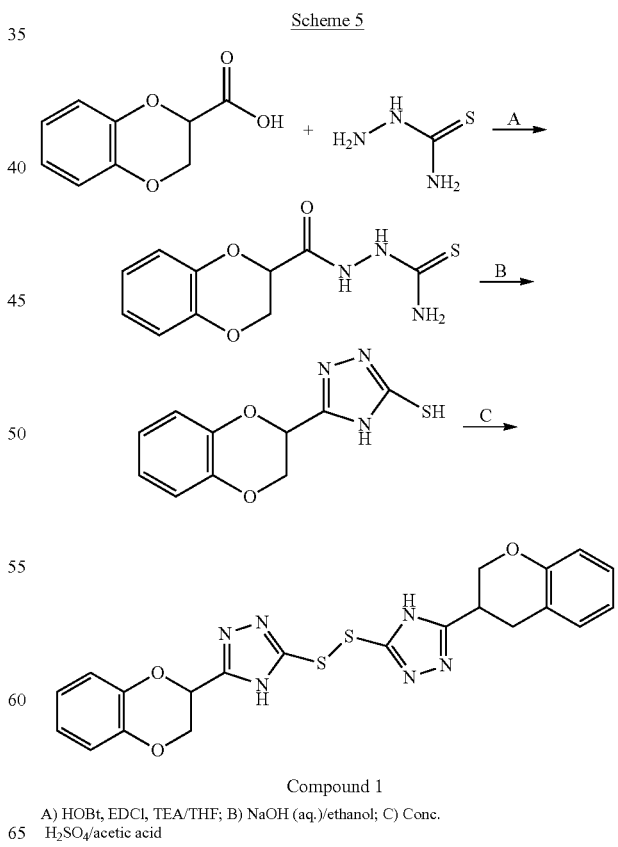

Compound 1
A) HOBt, EDCl, TEA/THF; B) NaOH (aq.)/ethanol; C) Conc. H$_2$SO$_4$/acetic acid Pharmaceutical Compositions When employed as pharmaceuticals, the compounds described herein can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), sublingual, transcutaneous, intrathecal, oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds described herein may be milled using known milling procedures such as wet milling to obtain a particle size appropriate for tablet formation and for other formulation types. Finely divided (nanoparticulate) preparations of the compounds described herein can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

In some embodiments, the composition is a sustained release composition comprising at least one compound described herein, or a pharmaceutically acceptable salt thereof, and at least one pharmaceutically acceptable carrier. In some embodiments, the composition comprises at least one compound described herein, or a pharmaceutically acceptable salt thereof, and at least one component selected from microcrystalline cellulose, lactose monohydrate, hydroxypropyl methylcellulose, and polyethylene oxide. In some embodiments, the composition comprises at least one compound described herein, or a pharmaceutically acceptable salt thereof, and microcrystalline cellulose, lactose monohydrate, and hydroxypropyl methylcellulose. In some embodiments, the composition comprises at least one compound described herein, or a pharmaceutically acceptable salt thereof, and microcrystalline cellulose, lactose monohydrate, and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel K00LV™). In some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

The compositions can be formulated in a unit dosage form, each dosage containing from about 5 to about 1,000 mg (1 g), more usually about 100 mg to about 500 mg, of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the invention contain from about 5 mg to about 50 mg of the active ingredient. One having ordinary skill in the art will appreciate that this embodies compounds or compositions containing about 5 mg to about 10 mg, about 10 mg to about 15 mg, about 15 mg to about 20 mg, about 20 mg to about 25 mg, about 25 mg to about 30 mg, about 30 mg to about 35 mg, about 35 mg to about 40 mg, about 40 mg to about 45 mg, or about 45 mg to about 50 mg of the active ingredient.

In some embodiments, the compositions of the invention contain from about 50 mg to about 500 mg of the active ingredient. One having ordinary skill in the art will appreciate that this embodies compounds or compositions containing about 50 mg to about 100 mg, about 100 mg to about 150 mg, about 150 mg to about 200 mg, about 200 mg to about 250 mg, about 250 mg to about 300 mg, about 350 mg to about 400 mg, or about 450 mg to about 500 mg of the active ingredient.

In some embodiments, the compositions of the invention contain from about 500 mg to about 1,000 mg of the active ingredient. One having ordinary skill in the art will appreciate that this embodies compounds or compositions containing about 500 mg to about 550 mg, about 550 mg to about 600 mg, about 600 mg to about 650 mg, about 650 mg to about 700 mg, about 700 mg to about 750 mg, about 750 mg to about 800 mg, about 800 mg to about 850 mg, about 850 mg to about 900 mg, about 900 mg to about 950 mg, or about 950 mg to about 1,000 mg of the active ingredient.

The active compound may be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the invention. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds described herein can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

EXAMPLES

The compounds described herein can be prepared in a number of ways based on the teachings contained herein and synthetic procedures known in the art or modifications thereof. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

$^1$H- and $^{13}$C-NMR spectra were acquired at room temperature or 60° C. using a Bruker Avance III (300 MHz for $^1$H, 75 MHz for $^{13}$C). Chemical shifts were referenced to the residual solvent peaks in deuterated DMSO.

High resolution mass-spectrometry (HR-MS) spectra were acquired using a TOF-Agilent 6230 UHPLC/PDA/MS with an ESI source. The difference between the measured ion mass and the expected ion mass was less than 5 ppm.

Example 1

1,2-bis(5-(2,3-dihydrobenzo[b][1,4]dioxin-2-yl)-4H-1,2,4-triazol-3-yl)disulfane (1)

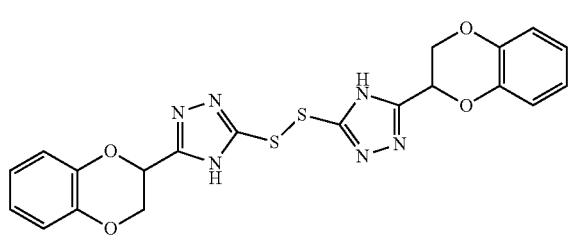 [SMILES: c1ccc2c(c1)OCC(c1nnc(SSc3nnc(C4COc5ccccc5O4)[nH]3)[nH]1)O2]

The title compound was prepared by Shanghai ChemPartner according to Scheme 5. Purity by analytical HPLC: 96%. HR-MS (ESI+): Calcd. Mw for $C_{20}H_{16}N_6O_4S_2$ 469.0675. found m/z 469.0748 [M+H]$^+$. The purity of compound 1 was determined using a 1200 Infinity Series analytical HPLC system (Agilent) operating at a flow rate of 0.9 mL/min, using a linear gradient of 2-98% acetonitrile in water (both solvents containing 0.1% v/v of ammonium hydroxide) over 2 min, on a Waters Acquity UPLC BEH C18 column (1.7 μm, 2.1×50 mm) set at 60° C.

Example 2

1,2-bis(5-(pyridin-4-yl)-4H-1,2,4-triazol-3-yl)disulfane (2)

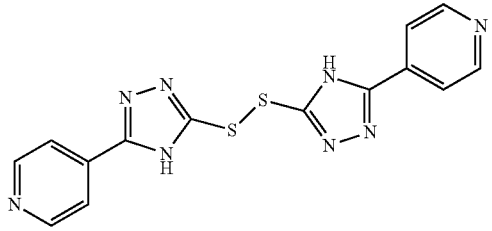 [SMILES: c1cc(-c2nnc(SSc3nnc(-c4ccncc4)[nH]3)[nH]2)ccn1]

Conc. $H_2SO_4$ (34 drops) was added to a suspension of 5-(pyridin-4-yl)-4H-1,2,4-triazole-3-thiol (256 mg, 1.43 mmol) in acetic acid (28 mL). After refluxing for 1 h, the reaction mixture was cooled to room temperature and the precipitate was collected, washed with ethanol, and dried under vacuum to give light yellow solid (Yield: 63.2%). LC-MS (ESI+): Calcd. mass for $C_{14}H_{10}N_8S_2$ 354.41. found m/z 355.84 [M+H]$^+$. (ESI−): Found m/z 353.95.

Example 3

3-(5-((5-(pyridin-4-yl)-4H-1,2,4-triazol-3-yl)disulfanyl)-4H-1,2,4-triazol-3-yl)pyridine (3)

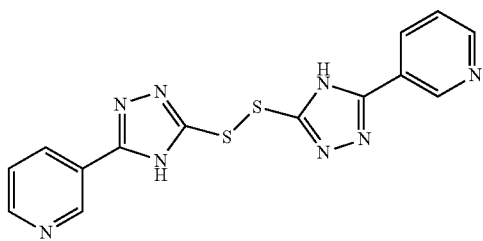 [SMILES: c1cncc(-c2nnc(SSc3nnc(-c4cccnc4)[nH]3)[nH]2)c1]

Conc. $H_2SO_4$ (34 drops) was added to a suspension of 5-(pyridin-4-yl)-4H-1,2,4-triazole-3-thiol (256 mg, 1.43 mmol) in acetic acid (28 mL). After refluxing for 3 h, the reaction mixture was cooled to room temperature and the precipitate was collected, washed with ethanol, and dried under vacuum to give light yellow solid (Yield: 56.9%).

LC-MS (ESI+): Calcd. mass for $C_{14}H_{10}N_8S_2$ 354.41. found m/z 355.84 [M+H]$^+$. (ESI−): Found m/z 354.02.

Example 4

1,2-bis(5-(furan-2-yl)-4H-1,2,4-triazol-3-yl)disulfane (4)

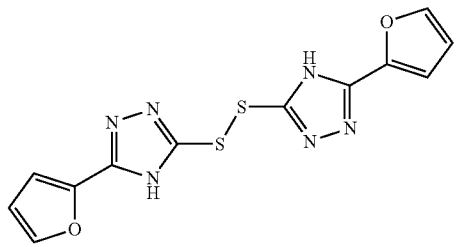 [SMILES: c1coc(-c2nnc(SSc3nnc(-c4ccco4)[nH]3)[nH]2)c1]

Conc. $H_2SO_4$ (17 drops) was added to a suspension of 5-(furan-2-yl)-4H-1,2,4-triazole-3-thiol (178 mg, 1 mmol)

in acetic acid (14 mL). After refluxing for 2 h, the reaction mixture was cooled to room temperature and the white precipitate was collected, washed with ethanol, and dried under vacuum (Yield: 61%).

LC-MS (ESI+): Calcd. mass for $C_{12}H_8N_6O_2S_2$ 332.36. found m/z 333.80 [M+H]$^+$. (ESI−): Found m/z 331.98.

Example 5

1,2-di(thiazol-2-yl)disulfane (5)

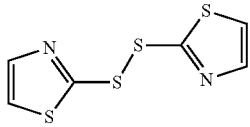 [SMILES: c1csc(SSc2nccs2)n1]

Hydrogen peroxide (30% in water, 150 μL) was added dropwise to a solution of 2-mercaptothiazole (0.26 g, 2.2 mmol) in ethanol (5 mL) and allowed to stir for 1 h at room temperature. The ethanol was subsequently evaporated, water was added to the mixture, and the suspension was filtered. The collected solids were dried under vacuum and recrystallized from hexane to give light yellow needles (Yield: 89%).

LC-MS (ESI+): Calcd. mass for $C_6H_4N_2S_4$ 232.37. found m/z 233.59 [M+H]$^+$. (ESI−): Found m/z 231.77.

Example 6

5,5'-disulfanediylbis(1,3,4-thiadiazol-2-amine) (6)

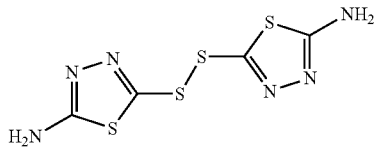

Hydrogen peroxide (150 uL) was added dropwise to a suspension of 2-amino-thiadiazine-5-thiol in (290 mg, 2.2 mmol) in ethanol (5 mL), followed by addition of $H_2SO_4$ (conc., 2 drops). The mixture was allowed to stir at room temperature for 1 h. The resulting precipitate was then collected and dried (Yield: 56%).

LC-MS (ESI+): Calcd. mass for $C_4H_4N_6S_4$ 264.37. found m/z 265.64 [M+H]$^+$. (ESI−): Found m/z 263.75.

Example 7

2,2'-disulfanediylbis(1H-imidazol-5-ol) (7)

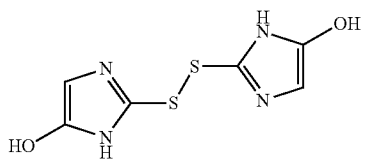

Thiohydantoin was dissolved in an aqueous solution of NaOH (0.11 g in 1 mL $H_2O$), followed by the dropwise addition of ammonium persulfate (0.16 g in 1 mL in water). The mixture was allowed to stir at room temperature for 1 h. The resulting solution was neutralized with HCl (6.25 N, 0.3 mL), affording an orange precipitate (Yield: 42%).

LC-MS (ESI+): Calcd. mass for $C_6H_6N_4O_2S_4$ 230.27. found m/z 229.67 [M+H]$^+$. (ESI−): Found m/z 227.85.

Example 8

$^1$H-NMR Data for Compounds 1-7

TABLE 1

$^1$H-NMR Data for Compounds 1-7

| # | $^1$H-NMR (300 MHz) |
|---|---|
| 1 | DMSO-$d_6$, 60° C.: δ 6.93-6.81 (m, 4H), 5.43 (bs, 1H), 4.50 (dd, J = 11.64, 2.55 Hz, 1H), 4.32 (dd, J = 11.64, 7.17 Hz, 1H) |
| 3 | DMSO-$d_6$: δ 14.96 (bs, 1H), 9.11 (d, J = 1.7 Hz, 1H), 8.64 (d, J = 4.0 Hz, 1H), 8.27 (dt, J = 8, 2 Hz, 1H), 7.52 (dd, J = 7.5, 5.0 Hz, 1H) |
| 4 | DMSO-$d_6$: δ 7.92 (m, 1H), 7.10 (d, J = 3.42 Hz, 1H), 6.71 (dd, J = 3.3, 1.8 Hz, 1H) |
| 5 | DMSO-$d_6$: δ 13.21 (bs, 1H), 7.28 (d, J = 4.4, 1H), 6.96 (d, J = 4.4 Hz, 1H) |
| 6 | DMSO-$d_6$: δ 7.74 (bs) |
| 7 | DMSO-$d_6$: δ 12.17 (bs), 11.85 (s, 1H), 10.25 (s, 1H), 4.60 (s, 1H) |

Example 9

$^{13}$C-NMR Data for Compounds 1-7

TABLE 2

$^{13}$C-NMR Data for Compounds 1-7

| # | $^{13}$C-NMR (75 MHz) |
|---|---|
| 1 | DMSO-$d_6$, RT: δ 160.6, 158.2, 154.4, 143.1, 142.7, 122.1, 117.6, 68.3, 65.7 |
| 3 | DMSO-$d_6$: δ 150.8, 147.0, 146.8, 133.6, 133.3, 124.2, 123.9 |
| 4 | DMSO-$d_6$: δ 155.9, 150.5, 144.9, 143.1, 112.2, 111.0 |
| 5 | DMSO-$d_6$: δ 155.9, 150.5, 144.9, 143.1, 112.2, 111.0. |
| 6 | DMSO-$d_6$: δ 172.6, 149.2. |
| 7 | DMSO-$d_6$: δ 183.8, 178.0, 172.4, 164.7, 114.8, 60.9. |

Example 10

Preparation of Hemoglobin

Outdated donated human red blood cells (RBCs) were obtained from the Blood Bank of Massachusetts General Hospital. The RBCs were centrifuged at 3,000 rpm for 15 min at 4° C. The supernatant was discarded, and the remaining RBCs were washed three times with an equal volume of 0.9% sodium chloride. Three equivalents of distilled water were added to the washed RBCs, and the mixture was centrifuged at 20,000 g for 1 h at 4° C. The supernatant was collected and centrifuged again under the same conditions. The resulting supernatant was collected and dialyzed against Dulbecco's phosphate buffered saline (DPBS, pH 7.4) at 4° C. After dialysis, the sample was sterilized by twice passing it through 2-μm filters to confirm that the solution would pass through smoothly.

The absorption spectrum of the hemoglobin solution was measured from 500-700 nm, and the absorption spectra were fitted to a linear combination of pure oxyHb, deoxyHb and metHb plus a baseline (least-squared fitting) using a program (Solver in Excel 2007, Microsoft) to determine the total concentration of hemoglobin.

Example 11

Identification of Small Molecules Binding to Hemoglobin Using SMMs

Test compounds were affixed to SMM slides with isocyanate-functionalized surfaces as described in Casalena et al., *Methods in molecular biology*, 2012, 803, 249-263. Pre-incubating the SMMs with albumin blocked non-specific binding of the compounds to SMMs. Compounds binding to hemoglobin were detected on the SMMs using a fluorescent dye-conjugated antibodies specific for hemoglobin. The assay was validated by confirming the binding of hemoglobin to 2,3-DPG affixed on SMMs.

Each slide contained 48 "blocks", and each block contained approximately 100 unique surface-immobilized small molecules. Compounds were printed in duplicate, and each slide was screened in duplicate, resulting in four replicates for every test compound. SMM slides were blocked by incubating them in a TBS-T solution (Tween 20, 0.01 vol %) containing bovine serum albumin (BSA, 0.1 wt %) for 30 min. The slides were rinsed with TBS-T buffer for 2 min and incubated in a TBS-T solution containing purified hemoglobin (1 μg/mL). The hemoglobin-treated slides were rinsed with TBS-T buffer for 2 min and incubated with a TBS-T solution containing an antibody directed against human hemoglobin (mouse-IgG, 0.25 μg/mL Catalog No. ab55081, Abcam) for 30 min. Antibody-treated slides were washed for 2 min with TBS-T buffer and then incubated with a secondary detection anti-mouse IgG antibody labeled with Cy5 fluorescent dye (0.2 μg/mL, Catalog No. A10524, Invitrogen) for 30 min, followed by washing three times with TBS-T and once with distilled water, and 2 min on a shaker. All incubations were performed at room temperature and on a shaker set at the lowest setting. Slides were scanned using GenePix 4200A (Molecular Devices) with excitation wavelengths of 635 nm.

Using SMM Hits-Analyzer software (Broad Institute), the measured fluorescent signal of the foreground of a given spot (F) was divided by its local background (B) resulting in a calculated F/B ratio for each spot on which the test compounds were affixed. The F/B ratios were fitted to a Cauchy distribution plot for every block on the slide, and "positive" hits were determined using a p-value threshold of 7%. If all four "positive" replicates had p-values below 7%, they were selected as "hit" compounds binding to hemoglobin. An antibody counter screen was performed to exclude false positives that could be binding antibodies used in the testing, rather than the hemoglobin target.

Example 12

Screening of Small Molecules Altering Oxygen Binding Affinity of Hemoglobin

Sample Preparation for Hemoglobin Oxygen Binding Assay

Test compounds (0.75 μL, 10 mM in DMSO) were added to the central area of two 384 deep well plates forming compound plates. DPBS was used as the solvent for myo-inositol hexaphosphate (IHP) and N-ethylmaleimide (NEM) (10 mM). To prevent oxidation of hemoglobin during the experiment, glucose-6-phosphate (0.4 mg/mL), glucose-6-phosphate dehydrogenase (1.0 U/mL), nicotinamide adenine dinucleotide phosphate (NADP, 0.05 mg/mL), ferredoxin (0.01 mg/mL), ferredoxin-NADP reductase (0.01 U/mL) and catalase ($2\times10^3$ U/mL) were added to hemoglobin to produce the Hayashi reducing system, which is described in detail in Hayashi et al., *Biochemica et Biophysica Acta*, 1973, 310, 309-316.

The DPBS solution containing hemoglobin (10 μM) with the Hayashi reducing system (125 μL/well) was dispensed into the test compound plates, and the plates were shaken at 800 rpm for 3 min and centrifuged at 1,000 rpm for 1 min. The mixture of hemoglobin with each compound (50 μL/well) in the compound plates was transferred to four 384 well plates serving as the assay plates. The final concentration of hemoglobin, test compound and DMSO was 10 μM, 60 μM and 5 vol %, respectively.

Design of Hemoglobin Oxygen-Binding Assay

The alteration of hemoglobin's oxygen-binding affinity by the test compounds binding to hemoglobin was evaluated in an environment where the fractional oxygen pressure ($FO_2$) could be precisely measured and controlled. The assay was validated by measuring oxyHb % with and without two known allosteric effectors, myo-inositol hexaphosphate (IHP) and N-ethylmaleimide (NEM), at an allosteric effector to hemoglobin tetramer concentration of 6 to 1 (mol/mol). The IHP-induced decrease and NEM-induced increase of oxyHb % were consistent with their known ability to shift oxygen dissociation curves (ODCs) of hemoglobin. To confirm the allosteric effect of the test compounds, ODC of hemoglobin was measured in the presence and absence of each compound. The value of $P_{50}$ (the oxygen pressure at which the oxyHb level is 50%) was evaluated as a parameter of oxygen binding affinity.

The ability of small molecules to alter the oxygen affinity of hemoglobin was determined by measuring the fraction of oxygenated hemoglobin (oxyHb %) and oxidized hemoglobin (metHb %) using spectrophotometry under three (high, medium, and low oxyHb saturation) conditions. Hemoglobin was mixed with test compounds, and the mixture was added to 240 central wells of 384-well plates (50 μL/well). The concentrations of hemoglobin, compound, and dimethyl sulfoxide (DMSO) were 10 μM, 60 μM, and 5 vol % in Dulbecco's phosphate buffered saline (DPBS), respectively.

To control the environment, a plate reader (MultiSkan GO, Thermo Fisher Scientific), a plate shaker, thermometer, and a calibrated oxygen pressure meter were placed in a chamber (AtmosBag, Sigma). The $FO_2$ in the chamber was controlled by purging and then continuously providing a precise mixture of nitrogen and air into the chamber and was monitored via the oxygen pressure meter. Gas cylinders of nitrogen gas and air were connected to a gas proportioner to adjust the flow rate of nitrogen gas and air to the chamber. The gas proportioner was connected to a humidifier to maintain 70-85% humidity within the chamber, and the humidifier was connected to the gas inlet of the chamber. A gas outlet allowed gas release at atmospheric pressure.

The developed oxygen binding assay allows for a large number of assays to be conducted simultaneously with only small quantities of test molecules (12 nmoles per well).

Measurement of the Alteration of Oxygen-Binding Affinity Using the Hemoglobin-Oxygen Binding Assay Assay plates were transferred into the aforementioned chamber and equilibrated at three stepwise descending oxygen pressures at 25-27° C. For the highest saturation condition of oxygenated hemoglobin, the assay plates were incubated without shaking at $FO_2=1.2\%$ for 12 h, and visible absorption spectra of the samples were measured from 500 nm to 700 nm at 2 nm steps using the plate reader. After the measurement of the absorption spectra, the test plates were shaken for 1 h at $FO_2=1.2\%$ and the spectra were re-measured to obtain the medium oxygen saturation condition. The $FO_2$ was then reduced to 0.5% and the plates were shaken for 1 h. The spectra were then measured to obtain the lowest saturation condition. To determine the fraction of oxyhemoglobin saturation (oxyHb %) of each sample, the measured absorption spectra were analyzed by least-squared fitting to determine oxyHb % and metHb % using Solver (Microsoft Excel 2007).

Statistical Analysis

In the hemoglobin-oxygen binding assay, an uneven distribution of oxyHb % between the wells of each plate was observed when oxyHb % without compounds was measured. To account for the uneven oxygenation distribution, a calibration factor was introduced for each well. To determine the calibration factor, hemoglobin was added to the central 240 wells, and the plate was replicated to four plates. Absorption spectra were measured at the assay saturation conditions and oxyHb % was determined by the least-squared fitting. The calibration factor was determined for each of the 240 wells at all three saturation conditions (highest, medium and lowest oxyHb %). For the selection of compounds altering oxyHb saturation, the value of oxyHb % was defined as the sum of oxyHb % calculated by the spectral deconvolution and the calibration factor.

The Z score for oxyHb % containing a unique compound ($Z_{oxy}$) was calculated according to Equation 1. In Equation 1, oxyHb $\%_{cpd}$ is oxyHb % containing a unique compound, and oxyHb $\%_{ctrl}$ is oxyHb % without any compound.

Equation 1. Z-Score for oxyHb % Containing a Unique Compound $Z_{oxy}$=(Mean value of oxyHb $\%_{ocpd}$–Mean value of oxyHb $\%_{ctrl}$)/Standard deviation of oxyHb $\%_{ctrl}$ The Z score was also calculated for metHb ($Z_{met}$) according to Equation 2. In Equation 2, metHb $\%_{cpd}$ is metHb % containing a unique compound, and metHb $\%_{cpd}$ is metHb % without any added compound. Compounds with (1) both $Z_{oxy}>2.5$ (increase of oxyHb %) and $Z_{met}<2.5$ or (2) both $Z_{oxy}<-2.5$ (decrease of oxyHb %) and $Z_{met}<2.5$ were selected as hit compounds that alter oxyHb % without increasing metHb formation.

Equation 2. Z-Score for metHb (%)

$Z_{met}$=(Mean value of metHb $(\%)_{cpd}$–Mean value of metHb $(\%)_{ctrl}$)/Standard deviation of metHb $(\%)_{ctrl}$ Example 13

Measurement of Oxygen Dissociation Curve (ODC)

The ODC of hemoglobin was measured with a HEMOX analyzer (TCS Scientific Corporation) at 37° C. For experiments with purified hemoglobin, hemoglobin (20 μM as tetramer) was dissolved in DPBS and antifoam (0.2 vol %, Catalog No. AFA-25, TCS Scientific Corporation) was added to prevent foaming of the sample. Compounds were prepared in DMSO stock solutions then added to hemoglobin. The final concentration of DMSO was adjusted to 5 vol %. For experiments with RBCs, blood was drawn from volunteers into EDTA tubes. The blood was centrifuged for 15 min at 3,000 rpm at 4° C. The supernatant was discarded, and RBCs were washed three times with DPBS, pH 7.4 by dilution to 50% hematocrit. The washed RBCs were then diluted with Hemox solution (mixture of N-[Tris(hydroxymethyl)methyl]-2-aminoethanesulfonic acid (TES, 30 mM), sodium chloride (135 mM), and potassium chloride (5 mM) in water (pH 7.4), TCS Scientific Corporation), and mixed with the compound stock solutions. When known allosteric effectors NEM (400 μM), 5HMF (2 mM) or formamidine disulfide (400 μM) were mixed with red blood cells for 1 h at 37° C., $P_{50}$ was reduced to 8 Torr, 9 Torr, and 9 Torr respectively, which correlated with previous reports (see Garel et al., *European Journal of Biochemistry*, 1982, 123, 513-519).

Example 14

Measurement of the ODC of Hemoglobin (Hb)+Compound 1

Figure 2A:
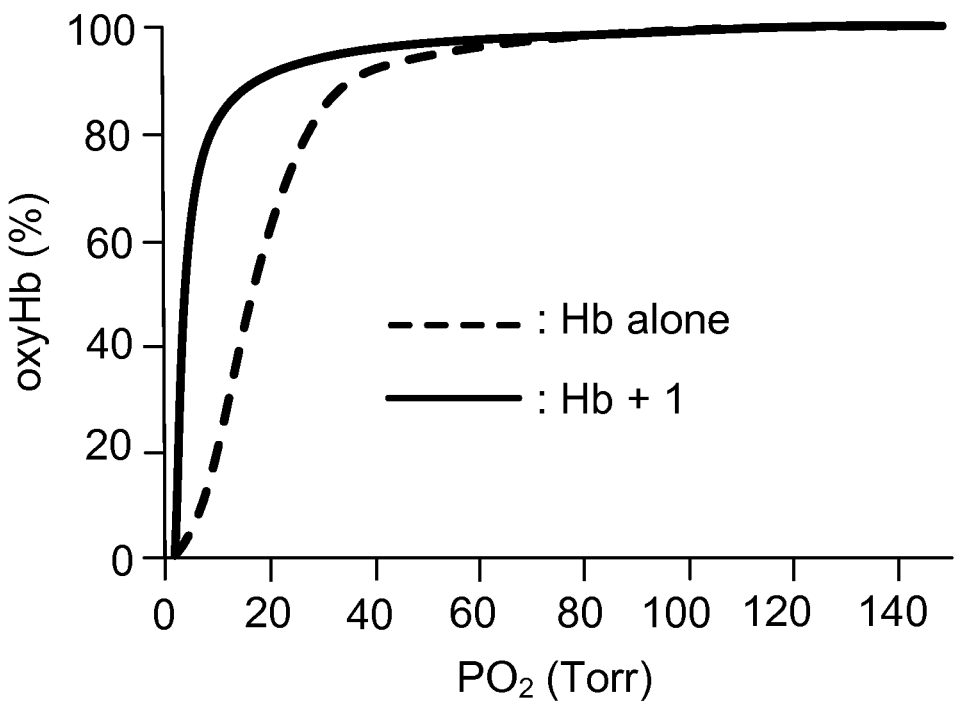
FIG. 2A shows an ODC of hemoglobin (20 μM as tetramer) with 1,2-bis(5-(2,3-dihydrobenzo[b][1,4]dioxin-2-yl)-4H-1,2,4-triazol-3-yl)disulfane (Compound 1) (120 μM) in DPBS (pH 7.4) with 5 vol % DMSO at 37° C. ODC was measured 10 min after mixing the compound with hemoglobin at 37° C. The $P_{50}$ of hemoglobin with and without Compound 1 are 4.2 and 17 Torr respectively.
Figure 2B:
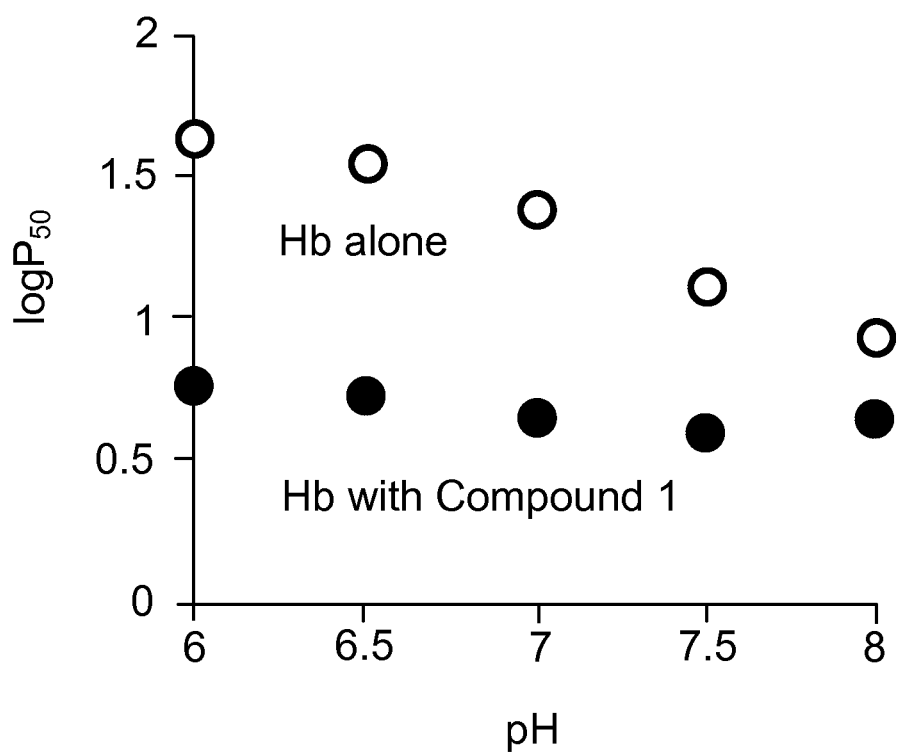
FIG. 2B shows the relationship between pH and $P_{50}$ of hemoglobin (20 μM) with and without addition of Compound 1 (120 μM) in 0.1 M phosphate buffer (pH 6-8) with 5 vol % DMSO at 37° C.

The ODC of hemoglobin with Compound 1 was measured to determine the increase of oxygen binding affinity of hemoglobin (FIG. 2A). When hemoglobin (20 μM as tetramer) was mixed with Compound 1 (120 μM) for 10 min at 37° C., the ODC was shifted to the left, and $P_{50}$ was markedly reduced to 4.2±0.1 Torr (shown as mean value±SD (N=3)) from 17±0.3 Torr (hemoglobin alone, p<0.001). Incubation of hemoglobin with Compound 1 reduced the Bohr effect (the increase of the $P_{50}$ of hemoglobin induced by decreasing the pH). ($\Delta \log P_{50}$)/$\Delta$pH was $-0.08\pm0.02$ vs $-0.37\pm0.04$, with and without Compound 1, (at a 6:1 molar ratio of Compound 1 to hemoglobin), respectively (P<0.001, FIG. 2B).

Figure 5A:
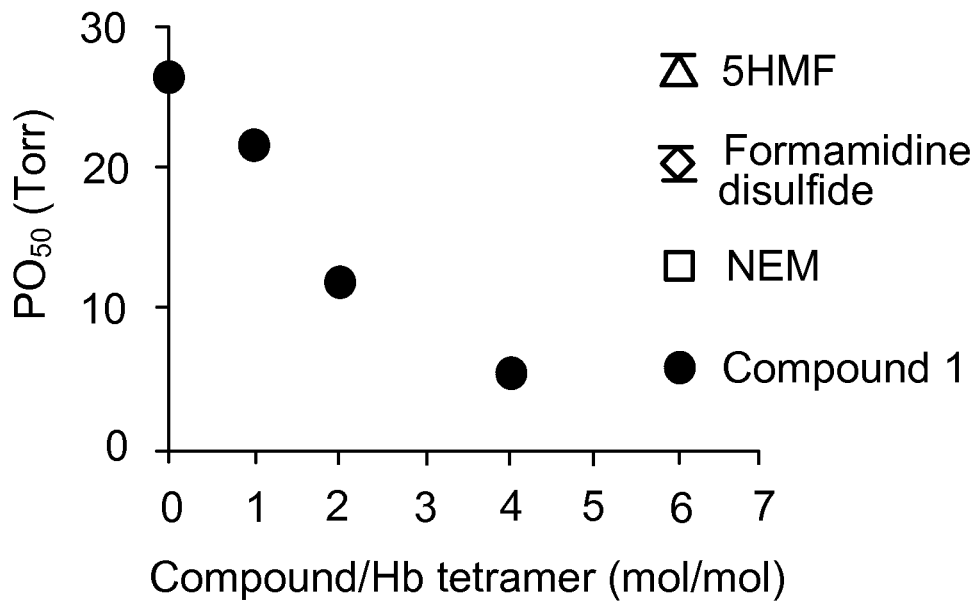
FIG. 5A shows a dose response of $P_{50}$ of RBCs on Compound 1 compared with 5-(Hydroxymethyl)furfural (5HMF), diformamidine disulfide and N-ethylmalaimide (NEM). Error bars represent standard deviation (N=3).
Figure 5B:
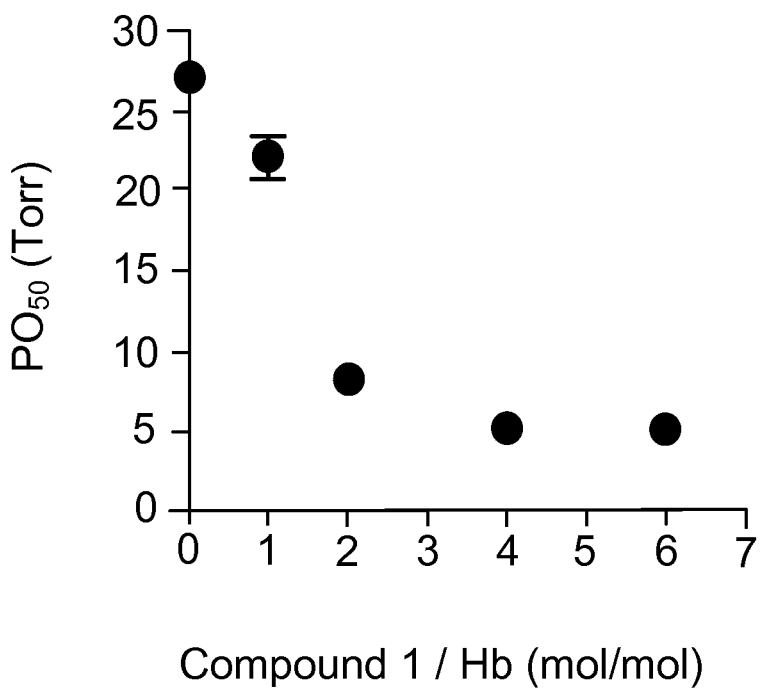
FIG. 5B shows the $P_{50}$ of whole blood without Compound 1 and with Compound 1 at 20, 40, 80, and 120 µM.
Figure 5C:
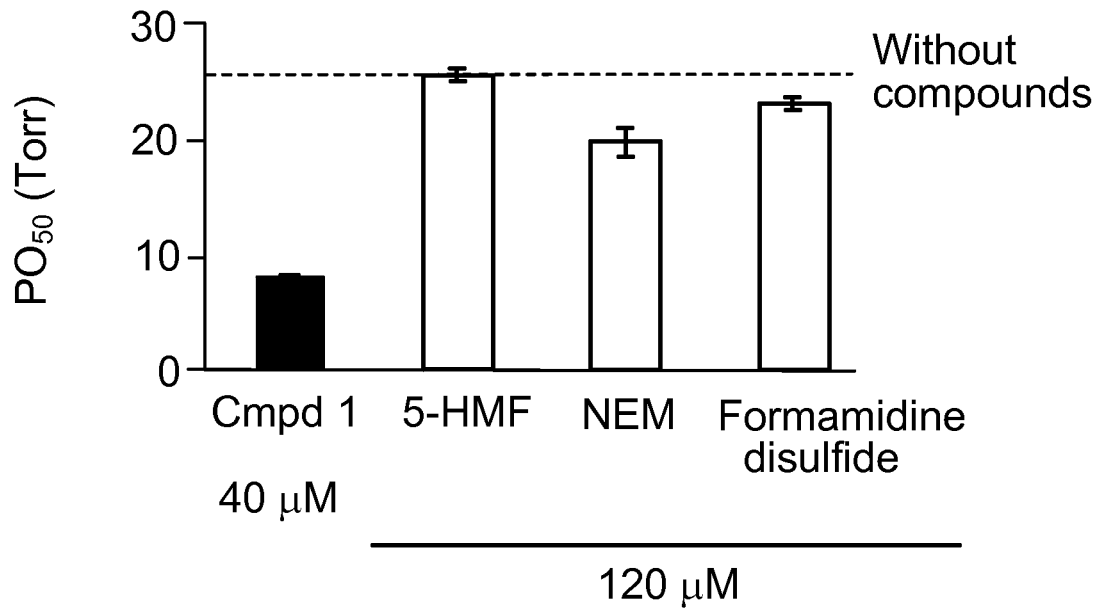
FIG. 5C shows the $P_{50}$ of whole blood mixed with Compound 1 (40 µM), 5-HMF (120 µM), formamidine disulfide (120 µM), and NEM (120 µM).
Figure 6:
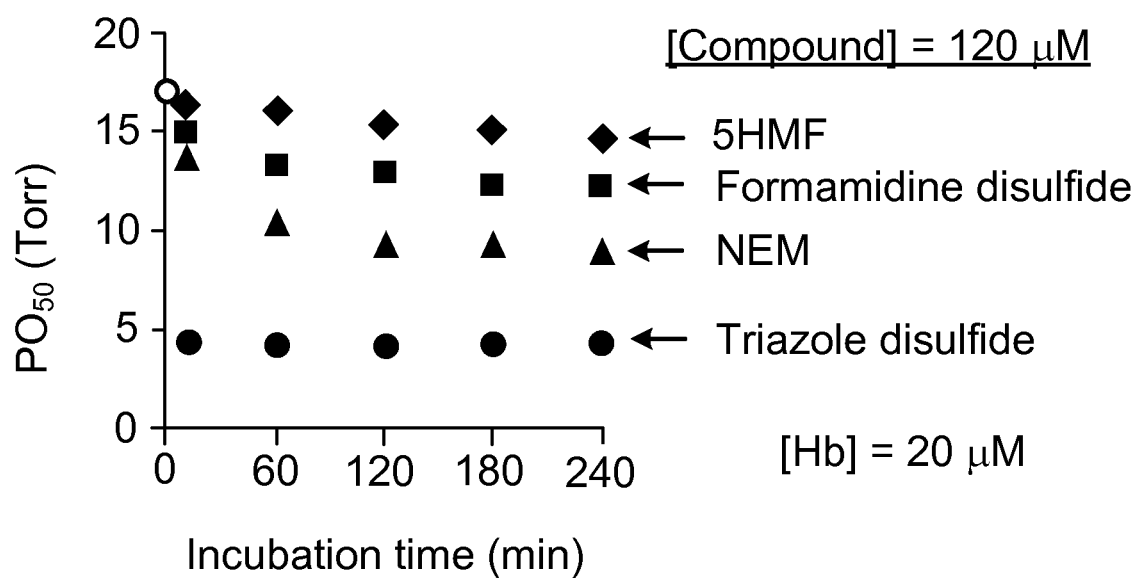
FIG. 6 shows a comparison of $P_{50}$ as a function of incubation time between Compound 1 (triazole disulfide) and known allosteric effectors 5HMF, formamidine disulfide, and NEM.

The decrease of $P_{50}$ induced by Compound 1 was also concentration-dependent (FIG. 5A-5B). The impact of Compound 1 on the ODC was dose-dependent with efficacy observed even when the ratio of compound to hemoglobin was 1:1 ($P_{50}$=22±1.4 Torr; P<0.001 vs without Compound 1; FIG. 5B). Compound 1 (40 μM) reduced the $P_{50}$ of whole blood greater than did other small molecules previously reported to increase the oxygen affinity of hemoglobin (FIG. 5C). For example, at a 6:1 molar ratio of compound to hemoglobin, 5-HMF did not change the $P_{50}$ ($P_{50}$=26±0.5 Torr), and NEM ($P_{50}$=20±1.1 Torr; P<0.001 vs 40 μM Compound 1) and diformamidine disulfide ($P_{50}$=23±0.6 Torr; P<0.001 vs 40 μM Compound 1) had only modest effects.

Figure 3:
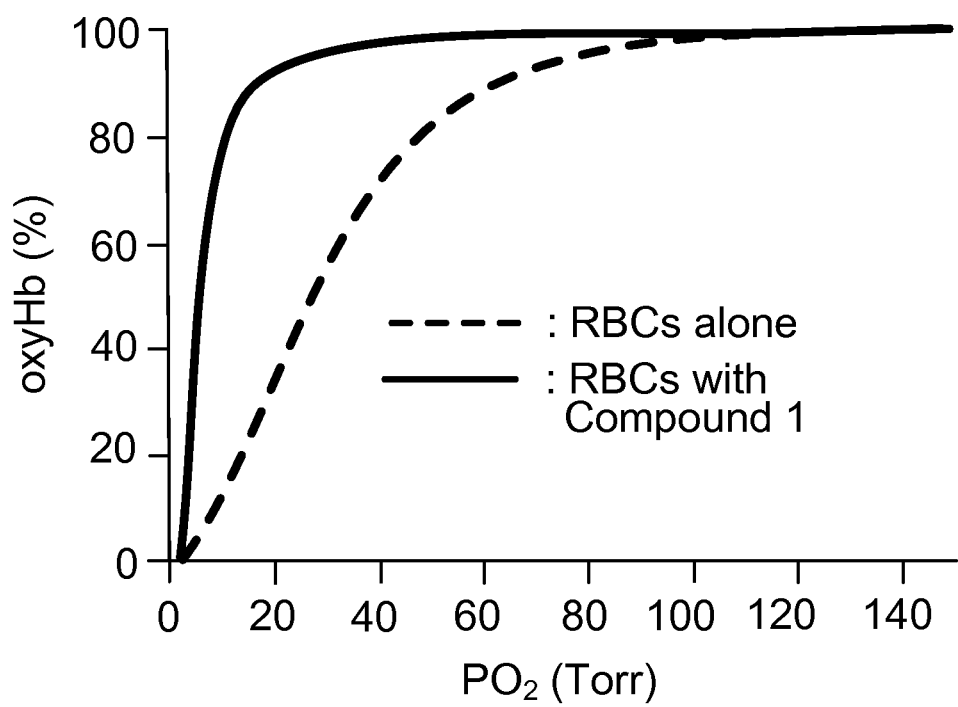
FIG. 3 shows an ODC of RBCs with Compound 1 (120 µM, six to one molar ratio to hemoglobin tetramer) in HEMOX solution with 5 vol % DMSO at 37° C. The $P_{50}$ of RBCs with and without Compound 1 are 5.7 and 26 Torr respectively.
Figure 4:
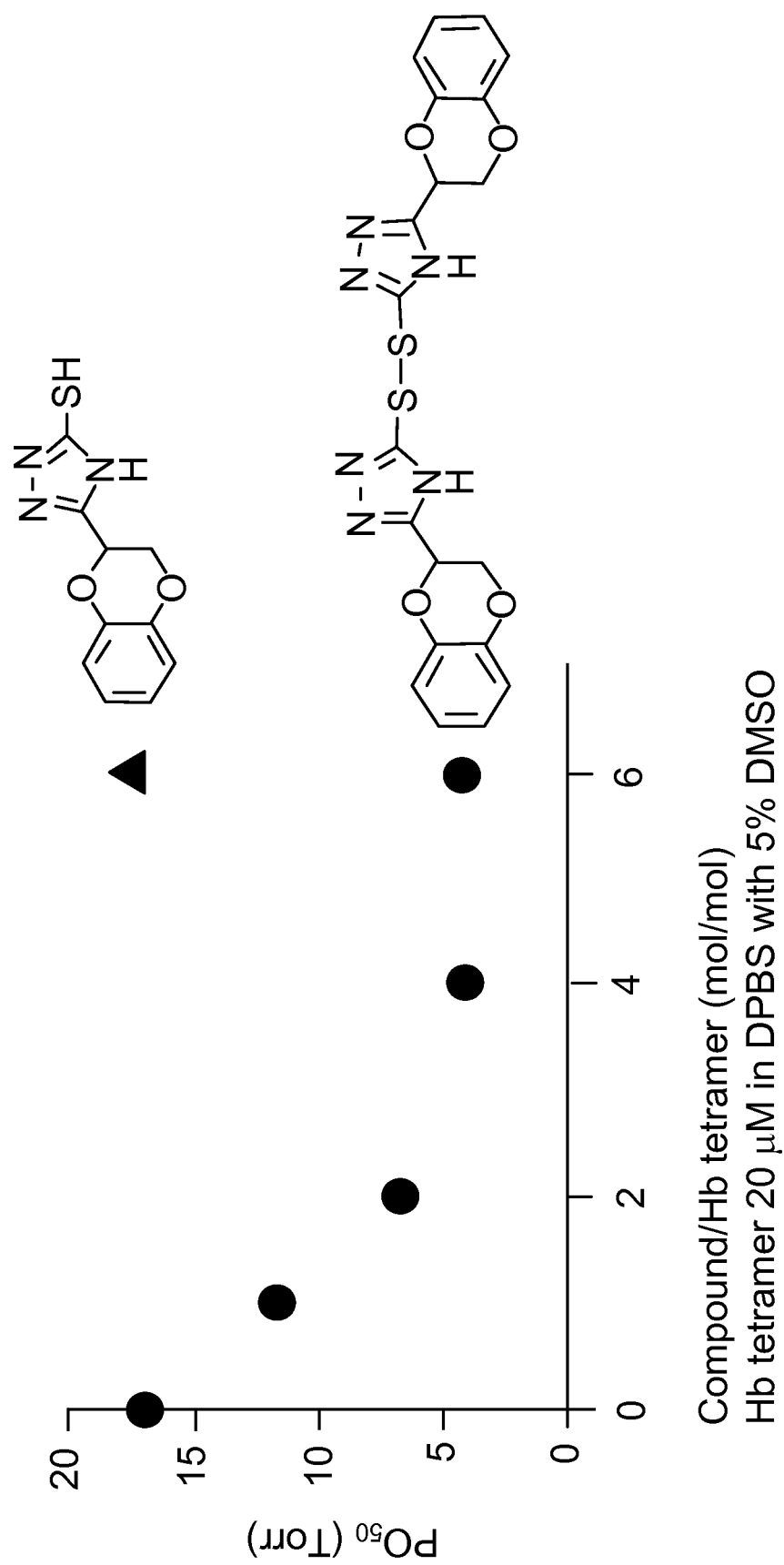
FIG. 4 shows a comparison of the effect on $P_{50}$ with Compound 1 and the corresponding thiol form (5-(2,3-dihydro-1,4-benzodioxin-2-yl)-4H-1,2,4-triazole-3-thiol). The thiol form does not alter $P_{50}$.

Compound 1 was found to be a more reactive allosteric effector than NEM, 5HMF, and formamidine disulfide (FIG. 7). For the reduction of $P_{50}$, less amount of 1 was needed, and the reaction time of 1 with hemoglobin was faster than NEM and 5HMF. Compound 1 (120 μM, six to one molar ratio to hemoglobin tetramer) also decreased the $P_{50}$ of human red blood cells from 26±1.1 Torr to 5.7±0.1 Torr (p<0.01, FIG. 3), while 5-HMF did not decrease the $P_{50}$ (27±0.5 Torr) at the same mixing time (10 min at 37° C.).

Data was analyzed by two-tailed, unpaired Student's t test using Microsoft Excel 2007. $P_{50}$ data for 19 representative compounds (purified hemoglobin and whole blood) are shown below in Table 3.

TABLE 3

P$_{50}$ Data of Example Compounds with purified hemoglobin and whole blood

| # | Compound Structure | Source | Solubility | P$_{50}$ of purified Hb | n50 | % met Hb | P$_{50}$ of whole blood |
|---|---|---|---|---|---|---|---|
| 1 | 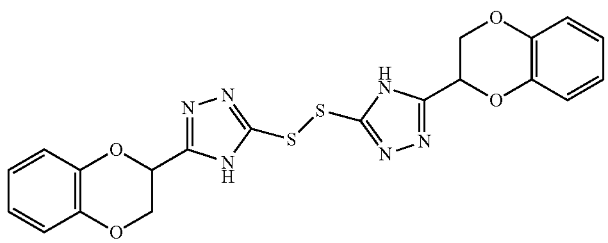 [SMILES: c1ccc2c(c1)OCC(c1nnc(SSc3nnc(C4COc5ccccc5O4)[nH]3)[nH]1)O2] | Commercial; purchased from ChemPartners | DMSO, PG (0.5M) PEG-400 (0.5M) | 4 | 2.23 | 5 | 6.06 |
| 2 | 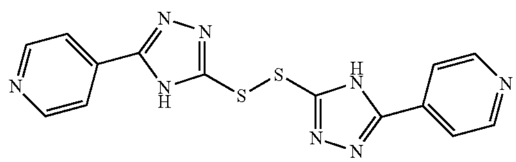 [SMILES: c1cc(-c2nnc(SSc3nnc(-c4ccncc4)[nH]3)[nH]2)ccn1] | Synthesized | DMSO, PBS (pH 2.5, <20 mM) | 4.94 | 2.7 | 4.2 | 10[a] |
| 3 | 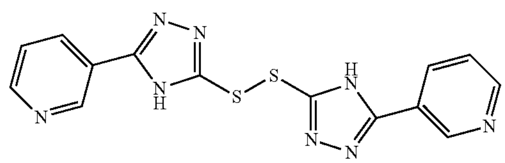 [SMILES: c1cncc(-c2nnc(SSc3nnc(-c4cccnc4)[nH]3)[nH]2)c1] | Synthesized | DMSO (60 mM) | 4.73 | 2.62 | 4.2 | 5.87[b] |
| 4 | 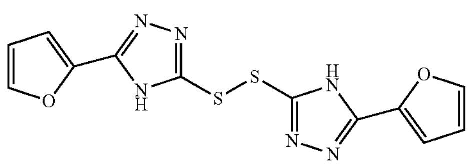 [SMILES: c1coc(-c2nnc(SSc3nnc(-c4ccco4)[nH]3)[nH]2)c1] | Synthesized | DMSO (1.5M) | 5.13 | 2.71 | 3.6 | 9.75 |
| 5 | 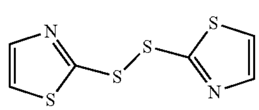 [SMILES: c1csc(SSc2nccs2)n1] | Synthesized | — | 7.88 | — | — | 13.95 |
| 6 | 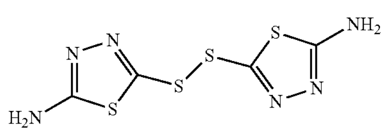 [SMILES: Nc1nnc(SSc2nnc(N)s2)s1] | Synthesized | DMSO | 5.35 | 2.71 | 4.1 | 13.79 |
| 7 | 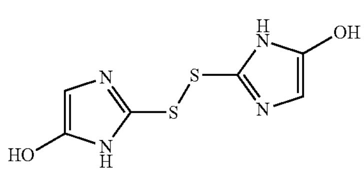 [SMILES: Oc1cnc(SSc2ncc(O)[nH]2)[nH]1] | Synthesized | — | 16.2 | — | — | N/T[c] |
| 8 | 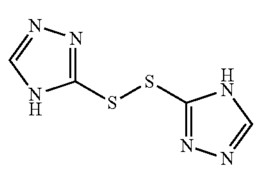 [SMILES: c1nnc(SSc2nnc[nH]2)[nH]1] | Commercial: Aldrich CPR R423955 | DMSO | 4.54 | 2.85 | 5.3 | 5 |
| 9 | 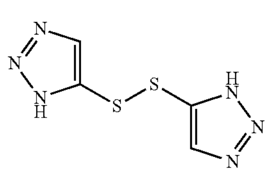 [SMILES: c1nn[nH]c1SSc1cnn[nH]1] | Commercial: TCI D3855 | DMSO, PG (0.5M) PEG-400 (0.5M) | 5.87 | 2.85 | 4.2 | 6.6 |

TABLE 3-continued

P$_{50}$ Data of Example Compounds with purified hemoglobin and whole blood

| # | Compound Structure | Source | Solubility | P$_{50}$ of purified Hb | n50 | % met Hb | P$_{50}$ of whole blood |
|---|---|---|---|---|---|---|---|
| 10 | 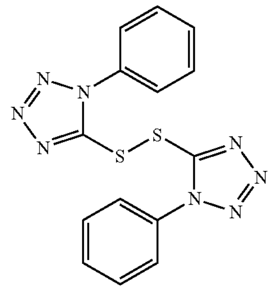 [SMILES: c1ccc(-n2nnnc2SSc2nnnn2-c2ccccc2)cc1] | Commercial: Aldrich CPR R423955 | DMSO | 16.85 | 2.81 | 1.7 | 29.22 |
| 11 | 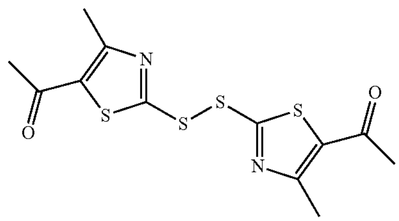 [SMILES: CC(=O)c1sc(SSc2nc(C)c(C(C)=O)s2)nc1C] | Commercial: Sigma PH002090 | DMSO | 15.01 | 2.3 | 5.4 | N/T |
| 12 | 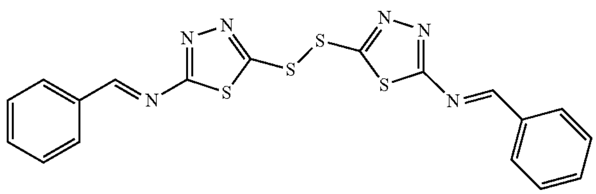 [SMILES: C(=N\c1nnc(SSc2nnc(/N=C/c3ccccc3)s2)s1)/c1ccccc1] | Commercial: Timtec ST509089182 | DMSO | 15.4 | 2.52 | 5.0 | N/T |
| 13 | 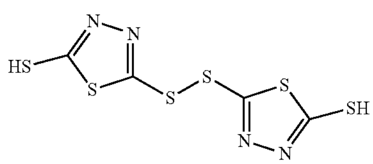 [SMILES: Sc1nnc(SSc2nnc(S)s2)s1] | Commercial: Sigma S275115 | DMSO - not completely soluble | 4.28$^d$ | 2.36 | 6.6 | N/T |
| 14 | 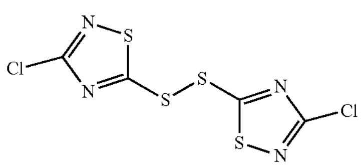 [SMILES: Clc1nsc(SSc2nc(Cl)ns2)n1] | Commercial: Oakwod chemical 024029 | DMSO | 10.2 | 1.75 | 7.5 | 24.65 |
| 15 | 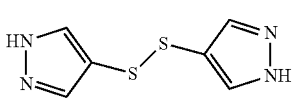 [SMILES: c1n[nH]cc1SSc1cn[nH]c1] | Commercial: Timtec ST50996992 (purchased as monohydrate) | DMSO | 15.6 | 2.65 | 1.7 | N/T |
| 16 | 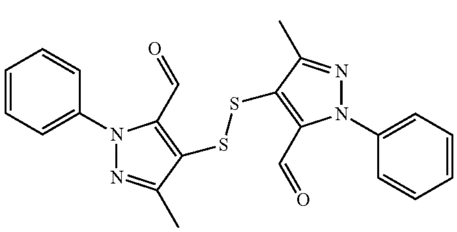 [SMILES: Cc1nn(-c2ccccc2)c(C=O)c1SSc1c(C)nn(-c2ccccc2)c1C=O] | Commercial: Timtec ST50989292 | DMSO | 9.4 | 2.3 | 5.3 | N/T |

TABLE 3-continued

P$_{50}$ Data of Example Compounds with purified hemoglobin and whole blood

| # | Compound Structure | Source | Solubility | P$_{50}$ of purified Hb | n50 | % met Hb | P$_{50}$ of whole blood |
|---|---|---|---|---|---|---|---|
| 17 | (bis(dimethylisoxazolyl) disulfide structure) | Commercial: Sigma-aldrich CCA005303 | DMSO | 5.91 | 2.4 | 5.2 | N/T |
| 18 | (bis(triethyl ester methylthiophene) disulfide structure) | Commercial: Sigma-aldrich S997080 | DMSO - not completely soluble | 16.37 | 2.87 | 3.3 | N/T |
| 19 | (bis(amino-triazolyl) disulfide structure) | Commercial: Sigma-aldrich CCA00895 | DMSO, PBS | 19 | — | — | 26.5 |

[a] After 1 h @ 37° C.
[b] causes some hemolysis
[c] N/T = not tested
[d] Compound was not very soluble
The concentration of hemoglobin and the added compound was 20 μM and 120 μM respectively.

Example 15

Anti-Sickling of Red Blood Cells

The pathophysiology of SCD is primarily driven by the polymerization of deoxyHbS (deoxygenated sickle hemoglobin). The morphological changes of red blood cells from sickle cell disease patients (SRBCs) were evaluated in the absence or presence of five different concentrations (0, 0.5, 1, 1.5 and 2 mM) of disulfide 1 in hypoxic condition (4% oxygen at 37° C. for 3 h). In the absence of 1, oxygenated SRBCs (FIG. 7A) were deoxygenated and polymerized to form sickle cells (FIG. 7B). The percentage of newly formed sickled cells was determined by subtracting the percentage of previously existing irreversibly sickled cells from the total percentage of sickled cells after incubation under 4% oxygen.

Figure 8:
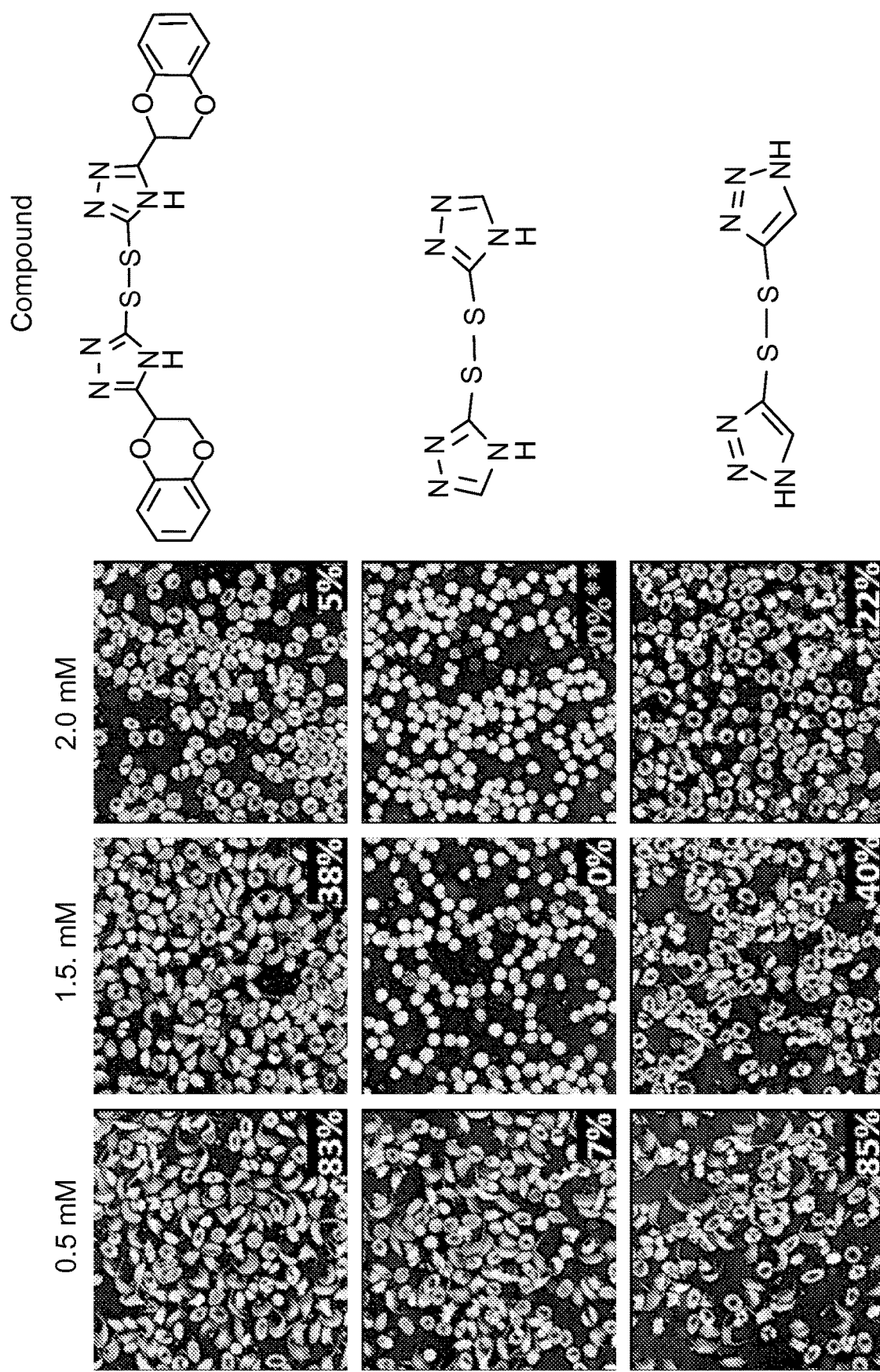
FIG. 8 shows the inhibition of red blood cell sickling in the presence of Compounds 1, 8, and 9 at 0.5 mM, 1.5 mM, and 2.0 mM.

In the absence of Compound 1, over 90% of SRBCs underwent sickling in 3 h (FIG. 7B) but the percentage of sickled cells decreased in a dose-dependent manner of Compound 1 (FIG. 7C-F). In SRBCs with 2 mM of Compound 1, almost 100% of red blood cells were not sickled under hypoxic conditions and appeared as oxygenated SRBCs (FIG. 7A). Compound 1 also increased oxygen binding affinity of hemolysates of SRBCs, and the P$_{50}$ of the hemolysates increased in a dose-dependent manner of 1 (FIG. 7G). Cell morphology in the presence of disulfides 1, 8, and 9, at 0.5 mM, 1.5 mM, and 2.0 mM are shown in FIG. 8.

The concentration of Compound 1 (2 mM) required to reduce sickling of hypoxic SS RBCs by nearly 90% was less than that reported for 5-HMF (5 mM). Moreover, it is conceivable that because of its covalent interactions with hemoglobin, Compound 1 may have a more sustained effect on oxygen affinity than do other allosteric effectors that do not form covalent bonds with hemoglobin. As a relevant corollary, these findings indicate that the binding of Compound 1 to hemoglobin in RBCs is not significantly blocked by plasma molecules including albumin when more than a 1:1 molar ratio of Compound 1 to hemoglobin is added to blood.

Example 16

Crystallization of Hemoglobin with Compound 1

To obtain liganded hemoglobin structure in complex with Compound 1, a freshly prepared solution of 1 in DMSO was incubated with oxygenated hemoglobin (oxyHb) for 1 h at 37° C. at a hemoglobin tetramer-1 molar ratio of 1:10. The mixture was then saturated with carbon monoxide (CO) to generate CO hemoglobin (COHb). Crystallization was performed with a solution of 20-30 mg/mL protein, 3.0-3.4 M sodium/potassium phosphate, at pH levels ranging from 6.4 to 7.6 using vacutainer tubes. One to two drops of toluene were added to each tube to facilitate crystallization. Additional CO was bubbled into the tubes which were then sealed. X-ray quality crystals were visible within 2-3 days, with the majority of crystals forming as long rectangular needles, typical of quaternary R3-state crystals. Trigonal bipyrimidal (octahedral) crystals were also observed, typical of quaternary R-state crystals. Prior to use in X-ray diffraction, the crystals were washed in a cryo-protectant solution containing 50 μL mother liquor and 10-15 μL glycerol. The needle crystals had the space group P4$_1$22 with approximate unit-cell constants of a=62 Å, b=62 Å and c=176 Å, and expectedly isomorphous to high-salt R3 crystal. The octahedral crystals had the space group P4$_1$2$_1$2 with typical cell dimensions of a=53 Å, b=53 Å and c=193 Å that are also isomorphous to high-salt R crystal. Both crystal formations contain 1 dimer (α1β1) per asymmetric unit.

Figure 9B:
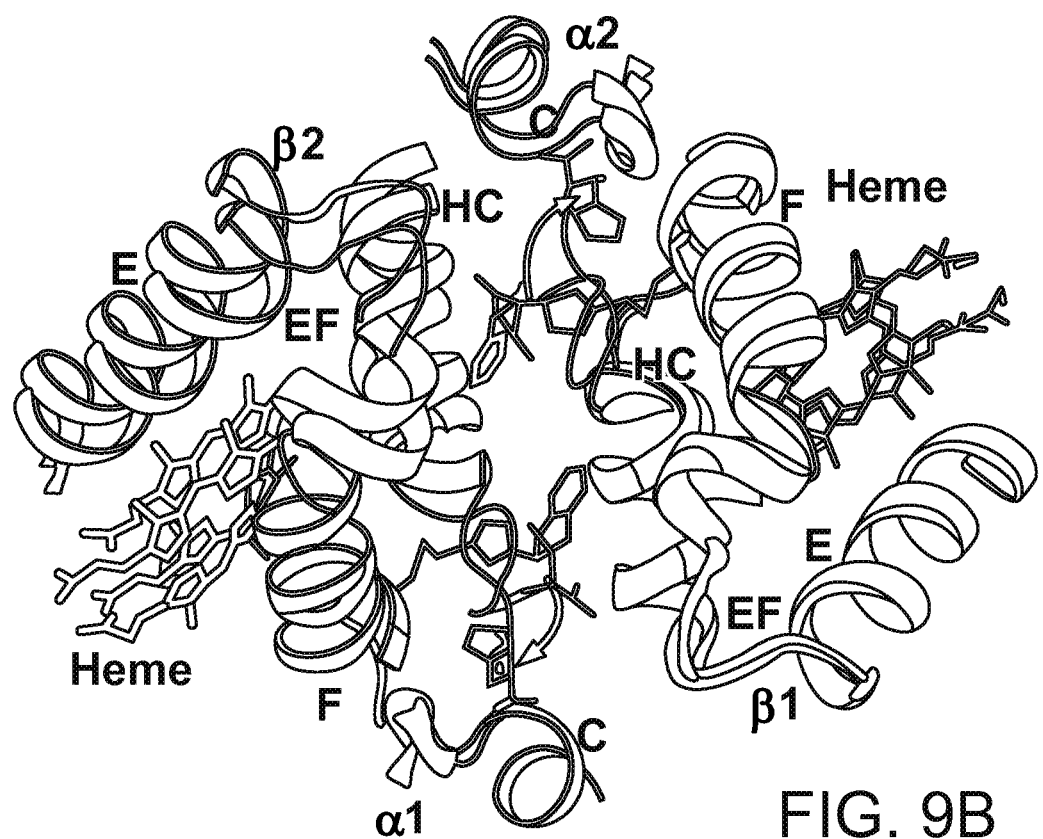
FIG. 9B depicts binding of MU-1/MU-1' (red sticks) to β-Cys93 (orange sticks) induces large tertiary and quaternary structural perturbations; hemoglobin in the absence of MUs (R3 state) is shown in gray and that in the presence of MUs is shown in green; magenta arrows represent the movement of β-His146 associated with MU-1/MU-1' binding of Cys93.
Figure 9C:
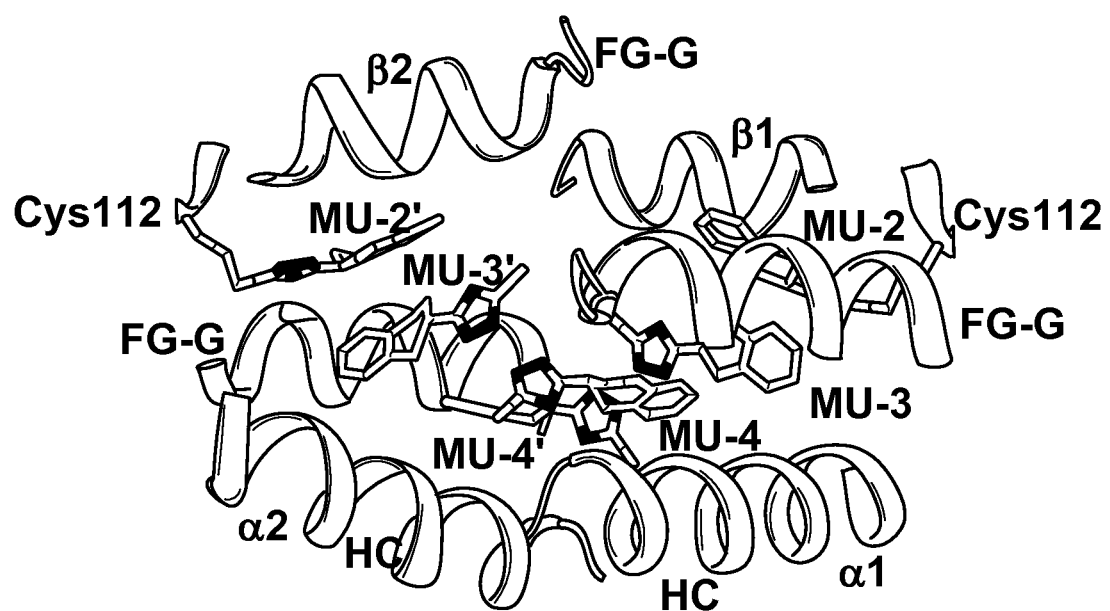
FIG. 9C depicts interactions of MU-2/MU-2', MU-3/MU-3', and MU-4/MU-4' in the water cavity tie the four hemoglobin subunits together.
Figure 9D:
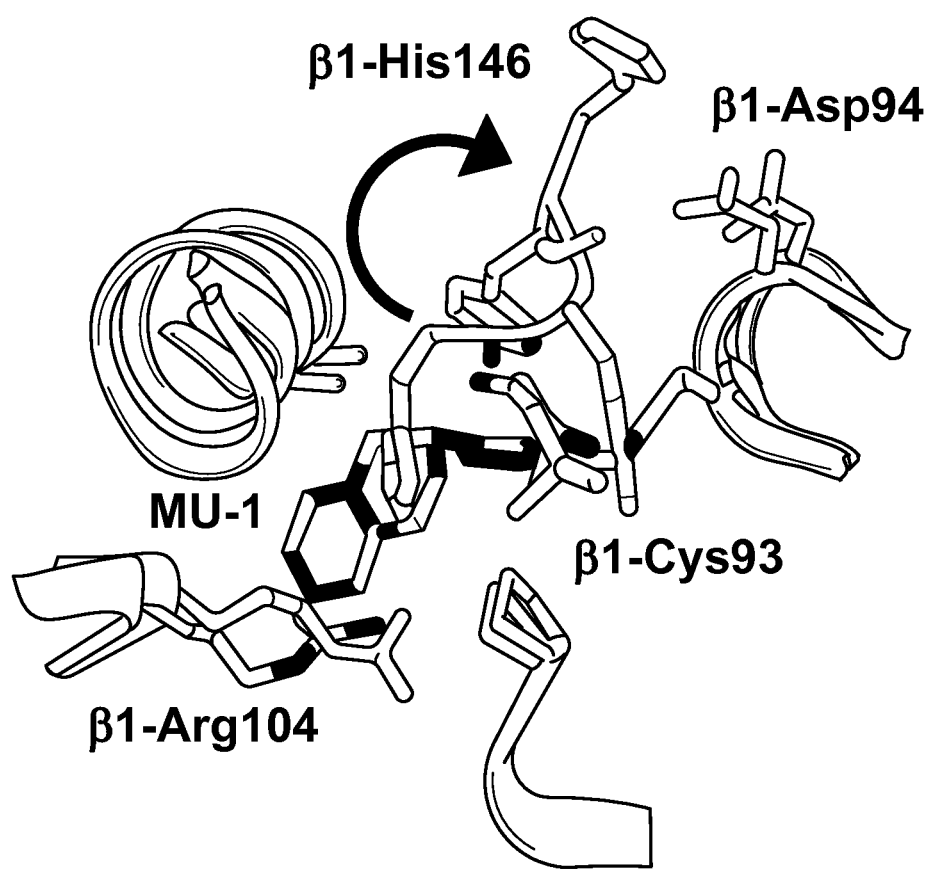
FIG. 9D depicts the superposition of COHb without MUs and the COHb-MU complex. MU-1 is shown as red sticks. The arrow represents the movement of β-His146 associated with MU-1/MU-1' binding of Cys93.

The tetramer structures of both the R and R3 revealed eight monomeric units (MU-1/MU-1'-MU-4/MU-4') of the divalent Compound 1 bound to hemoglobin (FIG. 9A-D). MU-1/MU-1' is located deep at the β-cleft and forms disulfide bond with β-Cys93 (FIG. 9C). Binding to β-Cys93 results in significant tertiary and quaternary structural changes in the R3 structure that include movement of the FG corner, F helix and the heme toward the interdimer interface, closer Fe-Fe distance, and narrower β-cleft and central water cavity (FIG. 9C). MU-2/MU-2' also forms a disulfide bond with β-Cys112 located at the central water cavity, where the rest of the MU molecules (MU-3/MU-3' and MU-4/MU-4') also bind non-covalently (FIG. 9B). Each of the six MU molecules (MU-2/MU-2', MU-3/MU-3' and MU-4/MU-4') binding in the water cavity makes at least one hydrophobic and/or hydrogen-bond contact with one another. The compounds occupy similar positions in the two structures, but the density maps indicate that the compounds bind weakly in the R structure relative to the R3 structure.

Diffraction data of all crystals were collected at 100 K with a Rigaku IV++ image plate detector using a CuKα X-rays (λ=1.54 Å) from a MicroMax-007 source fitted with Varimax Confocal optics (Rigaku, The Woodlands, Tex.). The datasets were processed with the d*trek software (Rigaku) and the CCP4 suite of programs.

Example 17

Structure Determination of COHb in Complex with Compound 1

To determine the structures of the R3 and R crystals, the isomorphous R3 (PDB code 1YZI) and R (PDB code 1LJW) structures (α1β1 dimer) were used as starting coordinates to refine the two structures, respectively, using CNS and Phenix refinement programs. Model building and correction were carried out using COOT. An initial difference map of the R3 structure (as hemoglobin dimer) identified four monomeric units (MUs) of the divalent Compound 1 and three toluene molecules (from the crystallization experiment), which were modeled in the structure and refined. Similar number of MU and two toluene molecules in the R structure were observed. Unlike the bound MUs in the R3 structure, the compounds seem to bind weakly to the R structure as evidenced from the electron densities. The final crystallographic R-factor and R-free were 22.8/25.9 and 20.7/25.9 for the R3 and R structures, respectively.

Example 18

Mechanism of Action of High Oxygen Binding Affinity of Hb+1

The high reactivity of Compound 1 for covalent binding to hemoglobin is likely due to its triazole ring, which stabilizes the MU dissociated from Compound 1. We observed covalent modification of hemoglobin by MU at β-Cys93 and β-Cys112 but not at α-Cys104. There are six cysteine amino acids in hemoglobin (α-Cys104, β-Cys93, and β-Cys112, and their symmetry-related pairs). β-Cys93 is exposed at the surface of hemoglobin in the oxygenated state, and β-Cys112 is located in the central water cavity, while α-Cys104 is buried in the protein's interior. β-Cys93 is known to react with reagents such as disulfides, maleimide, nitric oxide, p-hydroxymercuribenzoate (PMB) and methyl bromide. α-Cys104 and β-Cys112 have been considered relatively non-reactive, since these residues are believed to be inaccessible. However, both PMB and methyl bromide can react with all the cysteine residues of hemoglobin. These results indicate that compounds that access the central cavity can react with the thiol of β-Cys112 even though β-Cys112 is not exposed on the surface of hemoglobin.

The crystal structure of hemoglobin bound to TD-1 suggests two mechanisms by which TD-1 can increase the oxygen affinity of hemoglobin. First, covalent binding of MU to β-Cys93 displaces the position of β-His146, sterically preventing the salt-bridge interaction between β-His146 and β-Asp94 in the T-state. Prevention of this salt-bridge interaction both destabilizes the T-state and stabilizes the R-state with a concomitant increase in oxygen affinity and impairment of the Bohr effect. 38,39 A second mechanism by which TD-1 alters the oxygen affinity of hemoglobin is attributable to the binding of the six MUs in the central water cavity. Each of the six MUs makes hydrogen bond and/or hydrophobic interactions with the hemoglobin subunits and at least one other MU. These interactions help to tie all four hemoglobin subunits together, stabilizing the R state and restricting the subunit rotation that is required to transition to the T state.

TD-1 increased the oxygen affinity of hemoglobin in a manner different from other allosteric effectors, 5-HMF, and the bifunctional acylating agent bis(3,5-dibromosalicyl)-fumarate. Two 5-HMF molecules form a Schiff-base interaction with the two N-terminal α-Val1 nitrogen atoms at the α-cleft of hemoglobin in the R2-state, stabilizing the relaxed state to increase hemoglobin oxygen affinity. Bis(3,5-dibromosalicyl)fumarate spans the 2,3-DPG binding site of hemoglobin by cross-linking β-Lys82 to β$_2$-Lys82, and as expected in the presence of 2,3-DPG, the oxygen affinity of the cross-linked hemoglobin is increased due to blockade of the 2,3-DPG site. The locations of all eight MUs of Compound 1 are different from the 2,3-DPG binding site. 2,3-DPG binds at the β-cleft on the dyad axis, and preferentially stabilizes the T state of hemoglobin relative to the R state.

The contents of Nakagawa, et al., *Chem. Biol.*, 9:2318-2335 (2014) is incorporated herein by reference in its entirety.

A number of embodiments of the invention have been described. Nevertheless, it will be understood that various modifications may be made without departing from the spirit and scope of the invention. The references, patents, and patent applications supra are incorporated herein by reference in its entirety.

What is claimed is:
1. A method of improving tolerance to a low oxygen environment or treating a complication resulting from sickle cell disease in an individual in need thereof, comprising contacting red blood cells of said individual with a compound of Formula I:

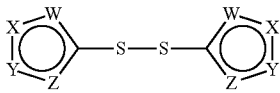

or a pharmaceutically acceptable salt thereof, wherein:
each W is independently selected from $CR^1$ and N;
each X is independently selected from $CR^2$ and N;
each Y is independently selected from $CR^3$, $NR^5$, N, S, and O;
each Z is independently selected from $CR^4$, $NR^6$, N, S, and O;
provided each

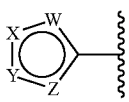

is, independently, a 5-membered heteroaryl ring, which does not contain any S—S, O—O, or S—O bonds; and provided that the selections for W, X, Y, and Z maintain proper valency;

each $R^1$, $R^2$, $R^3$, and $R^4$ are independently selected from H, —($C_{1-4}$ alkylene)-Cy, Cy, $C_{1-6}$ alkyl, $C_{2-6}$ alkenyl, $C_{2-6}$ alkynyl, $C_{1-6}$ haloalkyl, halo, CN, $NO_2$, $OR^a$, $SR^a$, $C(=O)R^a$, $C(=O)NR^cR^d$, $C(=O)OR^a$, $OC(=O)R^b$, $OC(=O)NR^cR^d$, $C(=NR^e)NR^cR^d$, $NR^cC(=NR^e)NR^cR^d$, $NR^cR^d$, $NR^cC(=O)R^b$, $NR^cC(=O)OR^a$, $NR^cC(=O)NR^cR^d$, $NR^cS(=O)R^b$, $NR^cS(=O)_2R^b$, $NR^cS(=O)_2NR^cR^d$, $S(=O)R^b$, $S(=O)NR^cR^d$, $S(=O)_2R^b$, $S(=O)_2NR^cR^d$, and $C=NR^f$; wherein $C_{1-6}$ alkyl, $C_{2-6}$ alkenyl, $C_{2-6}$ alkynyl, and $C_{1-6}$ haloalkyl are each optionally substituted by 1, 2, or 3 independently selected $R^x$ groups;

each $R^5$ and $R^6$ are independently selected from H, —($C_{1-4}$ alkylene)-Cy, Cy, $C_{1-6}$ alkyl, $C_{2-6}$ alkenyl, $C_{2-6}$ alkynyl, $C_{1-6}$ haloalkyl, $C(=O)R^a$, $C(=O)NR^cR^d$, $C(=O)OR^a$, $C(=NR^e)NR^cR^d$, $S(=O)R^b$, $S(=O)NR^cR^d$, $S(=O)_2R^b$, and $S(=O)_2NR^cR^d$; wherein $C_{1-6}$ alkyl, $C_{2-6}$ alkenyl, $C_{2-6}$ alkynyl, and $C_{1-6}$ haloalkyl are each optionally substituted by 1, 2, or 3 independently selected $R^x$ groups;

each Cy is independently selected from $C_{3-10}$ monocyclic or bicyclic cycloalkyl, 4-10 membered heterocycloalkyl, phenyl, naphthyl, and 5-10 membered heteroaryl, each of which is optionally substituted by 1, 2, 3, or 4 independently selected $R^x$ groups;

each $R^a$, $R^c$, and $R^d$ are independently selected from H, $C_{1-6}$ alkyl, $C_{2-6}$ alkenyl, $C_{2-6}$ alkynyl, $C_{1-6}$ haloalkyl, and Cy; wherein said $C_{1-6}$ alkyl, $C_{2-6}$ alkenyl, $C_{2-6}$ alkynyl, and $C_{1-6}$ haloalkyl are each optionally substituted with 1, 2, or 3 independently selected $R^x$ groups;

each $R^b$ is independently selected from $C_{1-6}$ alkyl, $C_{2-6}$ alkenyl, $C_{2-6}$ alkynyl, $C_{1-6}$ haloalkyl, and Cy; wherein said $C_{1-6}$ alkyl, $C_{2-6}$ alkenyl, $C_{2-6}$ alkynyl, and $C_{1-6}$ haloalkyl are each optionally substituted with 1, 2, or 3 independently selected $R^x$ groups;

each $R^e$ is independently selected from H, CN, OH, $C_{1-4}$ alkyl, $C_{1-4}$ alkoxy, $NO_2$, $C(O)(C_{1-4}$ alkyl), and $S(=O)_2(C_{1-4}$ alkyl);

each $R^f$ is independently selected from $C_{1-6}$ alkyl, $C_{1-6}$ haloalkyl, and Cy; wherein said $C_{1-6}$ alkyl and $C_{1-6}$ haloalkyl are each optionally substituted with 1, 2, or 3 independently selected $R^x$ groups;

each $R^x$ is independently selected from halo, OH, $NO_2$, CN, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonyloxy, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

2. The method of claim 1, where the method is a method of improving tolerance to a low oxygen environment in an individual in need thereof.

3. The method of claim 1, where the method is a method of treating a or complication resulting from sickle cell disease in an individual in need thereof.

4. The method of claim 1, wherein said contacting comprising administering the compound or salt to said individual.

5. The method of claim 3, wherein the complication resulting from sickle cell disease is sickle cell crisis.

6. The method of claim 3, wherein the complication resulting from sickle cell disease is selected from acute painful episodes, dactylitis, infection, overwhelming post-(auto)splenectomy infection (OPSI), anemia, acute chest syndrome, splenic sequestration, stroke, silent stroke, jaundice, infections, leg ulcers. bone damage, pulmonary hypertension, eye damage, organ failure, priapism, joint pain, cholelithiasis (gallstones), cholecystitis, avascular necrosis, osteomyelitis, acute papillary necrosis, background retinopathy, proliferative retinopathy, vitreous hemorrhages, retinal detachments, chronic renal failure, sickle cell nephropathy, neurocognitive decline, intracranial and intracerebral hemorrhage, transient ischemic attacks, infarctive stroke, spinal cord infarction or compression, vestibular dysfunction, sensory hearing loss, growth retardation, delayed puberty, splenic infarction, osteoporosis, bone marrow infarction and necrosis, bone marrow infarction with resulting exacerbation of anemia or pancytopenia, fat embolism, orbital compression syndrome, myocardial infarction, acute heptatic dysfunction, and pregnancy complications of mother or fetus.

7. The method of claim 1, wherein each

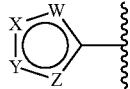

is a moiety of Formula (B):

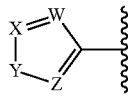

wherein:
each W is independently selected from $CR^1$ and N;
each X is independently selected from $CR^2$ and N;
each Y is independently selected from $NR^5$, S, and O; and
each Z is independently selected from $CR^4$ and N.

8. The method of claim 1, wherein each $R^1$ is independently selected from H, $C_{1-6}$ alkyl, and $C_{1-6}$ alkoxycarbonyl.

9. The method of claim 1, wherein each $R^2$ is independently selected from H, halo, and $C_{1-6}$ alkyl.

10. The method of claim 1, wherein each $R^3$ is independently selected from H, Cy, $OR^a$, $SR^a$, $C(=O)R^a$, $C(=O)OR^a$, $NR^cR^d$, and $C=NR^f$.

11. The method of claim 1, wherein each $R^5$ is independently selected from H and Cy.

12. The method of claim 1, wherein each $R^4$ is independently selected from H, $C_{1-6}$ alkyl, and $C(=O)R^a$.

13. The method of claim 1, wherein each $R^6$ is independently selected from H and Cy.

14. The method of claim 1, wherein each $R^a$, $R^c$, and $R^d$ are independently selected from H, $C_{1-6}$ alkyl, and $C_{1-6}$ haloalkyl; each $R^b$ is independently selected from $C_{1-6}$ alkyl and $C_{1-6}$ haloalkyl; and each $R^f$ is independently selected from $C_{1-6}$ alkyl, $C_{1-6}$ haloalkyl, and Cy.

15. The method of claim 1, wherein each

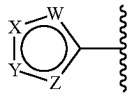

is a moiety of Formula (A) or (B):

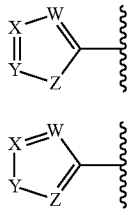

(A)

(B)

wherein:
each $R^1$ is independently selected from H, $C_{1-6}$ alkyl, $C_{1-6}$ haloalkyl, halo, CN, $OR^a$, $SR^a$, $C(=O)R^a$, $C(=O)NR^cR^d$, $C(=O)OR^a$, $NR^cR^d$, $NR^cC(=O)R^b$, $NR^cC(=O)OR^a$, $NR^cC(=O)NR^cR^d$, $NR^cS(=O)_2R^b$, $S(=O)_2R^b$, and $S(=O)_2NR^cR^d$;
each $R^2$ is independently selected from H, $C_{1-6}$ alkyl, $C_{1-6}$ haloalkyl, halo, and CN;
each $R^3$ is independently selected from H, Cy, $C_{1-6}$ alkyl, $C_{1-6}$ haloalkyl, halo, CN, $OR^a$, $SR^a$, $C(=O)R^a$, $C(=O)NR^cR^d$, $C(=O)OR^a$, $NR^cR^d$, $NR^cC(=O)R^b$, $NR^cC(=O)OR^a$, $NR^cC(=O)NR^cR^d$, $NR^cS(=O)_2R^b$, $S(=O)_2R^b$, $S(=O)_2NR^cR^d$, and $C=NR^f$;
each $R^5$ is independently selected from H, $C_{1-6}$ alkyl, $C_{1-6}$ haloalkyl, and Cy;
each $R^4$ is independently selected from H, $C_{1-6}$ alkyl, $C_{1-6}$ haloalkyl, halo, CN, $OR^a$, $SR^a$, $C(=O)R^a$, $C(=O)NR^cR^d$, $C(=O)OR^a$, $NR^cR^d$, $NR^cC(=O)R^b$, $NR^cC(=O)OR^a$, $NR^cC(=O)NR^cR^d$, $NR^cS(=O)_2R^b$, $S(=O)_2R^b$, and $S(=O)_2NR^cR^d$;
each $R^6$ is independently selected from H, $C_{1-6}$ alkyl, $C_{1-6}$ haloalkyl, and Cy;
each Cy is independently selected from $C_{3-7}$ monocyclic cycloalkyl, 4-10 membered heterocycloalkyl, phenyl, and 5-10 membered heteroaryl, each of which is optionally substituted by 1, 2, 3, or 4 independently selected $R^x$ groups;
each $R^a$, $R^c$, and $R^d$ are independently selected from H, $C_{1-6}$ alkyl, and $C_{1-6}$ haloalkyl;
each $R^b$ is independently selected from $C_{1-6}$ alkyl and $C_{1-6}$ haloalkyl; and
each $R^f$ is independently selected from $C_{1-6}$ alkyl, $C_{1-6}$ haloalkyl, and Cy;
provided that for Formula (A):
each W is independently selected from $CR^1$ and N;
each X is independently selected from $CR^2$ and N;
each Y is independently selected from $CR^3$ and N; and
each Z is independently selected from $NR^6$, S, and O; and
and provided that for Formula (B):
each W is independently selected from $CR^1$ and N;
each X is independently selected from $CR^2$ and N;
each Y is independently selected from $NR^5$, S, and O; and
each Z is independently selected from $CR^4$ and N.

16. The method of claim 1, wherein each

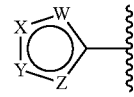

is a moiety of Formula (A) or (B):

(A)

(B)

wherein:
each $R^1$ is independently selected from H, $C_{1-6}$ alkyl, and $C_{1-6}$ alkoxycarbonyl;
each $R^2$ is independently selected from H, halo, and $C_{1-6}$ alkyl;
each $R^3$ is independently selected from H, Cy, $OR^a$, $SR^a$, $C(=O)R^a$, $C(=O)OR^a$, $NR^cR^d$, and $C=NR^f$;
each $R^5$ is independently selected from H and Cy;
each $R^4$ is independently selected from H, $C_{1-6}$ alkyl, and $C(=O)R^a$;
each $R^6$ is independently selected from H and Cy;
each Cy is independently selected from $C_{3-7}$ monocyclic cycloalkyl, 4-10 membered heterocycloalkyl, phenyl, and 5-10 membered heteroaryl, each of which is optionally substituted by 1, 2, 3, or 4 independently selected $R^x$ groups;
each $R^a$, $R^c$, and $R^d$ are independently selected from H, $C_{1-6}$ alkyl, and $C_{1-6}$ haloalkyl;
each $R^b$ is independently selected from $C_{1-6}$ alkyl and $C_{1-6}$ haloalkyl; and
each $R^f$ is independently selected from $C_{1-6}$ alkyl, $C_{1-6}$ haloalkyl, and Cy;

provided that for Formula (A):
  each W is independently selected from $CR^1$ and N;
  each X is independently selected from $CR^2$ and N;
  each Y is independently selected from $CR^3$ and N; and
  each Z is independently selected from $NR^6$, S, and O;
and
and provided that for Formula (B):
  each W is independently selected from $CR^1$ and N;
  each X is independently selected from $CR^2$ and N;
  each Y is independently selected from $NR^5$, S, and O; and
  each Z is independently selected from $CR^4$ and N.

17. The method of claim 1, wherein the compound is selected from:
  1,2-bis(5-(2,3-dihydrobenzo[b][1,4]dioxin-2-yl)-4H-1,2,4-triazol-3-yl)disulfane;
  1,2-bis(5-(pyridin-4-yl)-4H-1,2,4-triazol-3-yl)disulfane;
  1,2-bis(5-(pyridin-3-yl)-4H-1,2,4-triazol-3-yl)disulfane;
  1,2-bis(5-(furan-2-yl)-4H-1,2,4-triazol-3-yl)disulfane;
  1,2-di(thiazol-2-yl)disulfane;
  5,5'-disulfanediylbis(1,3,4-thiadiazol-2-amine);
  2,2'-disulfanediylbis(1H-imidazol-5-ol);
  1,2-di(4H-1,2,4-triazol-3-yl)disulfane;
  1,2-di(1H-1,2,3-triazol-5-yl)disulfane;
  1,2-bis(1-phenyl-1H-tetrazol-5-yl)disulfane;
  1,1'-(2,2'-disulfanediylbis(4-methylthiazole-5,2-diyl))diethanone;
  (NE,N'E)-5,5'-disulfanediylbis(N-benzylidene-1,3,4-thiadiazol-2-amine);
  5,5'-disulfanediylbis(1,3,4-thiadiazole-2-thiol);
  1,2-bis(3-chloro-1,2,4-thiadiazol-5-yl)disulfane;
  1,2-di(1H-pyrazol-4-yl)disulfane;
  4,4'-disulfanediylbis(3-methyl-1-phenyl-1H-pyrazole-5-carbaldehyde);
  1,2-bis(3,5-dimethylisoxazol-4-yl)disulfane;
  tetraethyl 5,5'-disulfanediylbis(3-methylthiophene-2,4-dicarboxylate); and
  5,5'-disulfanediylbis(4H-1,2,4-triazol-3-amine);
or a pharmaceutically acceptable salt thereof.

18. A method of improving tolerance to a low oxygen environment or treating a sickle cell disease and a complication resulting from sickle cell disease in an individual in need thereof, comprising contacting red blood cells of said individual with a compound selected from:
  1,2-bis(5-(2,3-dihydrobenzo[b][1,4]dioxin-2-yl)-4H-1,2,4-triazol-3-yl)disulfane;
  1,2-bis(5-(pyridin-4-yl)-4H-1,2,4-triazol-3-yl)disulfane;
  1,2-bis(5-(pyridin-3-yl)-4H-1,2,4-triazol-3-yl)disulfane;
  1,2-bis(5-(furan-2-yl)-4H-1,2,4-triazol-3-yl)disulfane;
  1,2-di(thiazol-2-yl)disulfane;
  5,5'-disulfanediylbis(1,3,4-thiadiazol-2-amine);
  2,2'-disulfanediylbis(1H-imidazol-5-ol);
  1,2-di(4H-1,2,4-triazol-3-yl)disulfane;
  1,2-di(1H-1,2,3-triazol-5-yl)disulfane;
  1,2-bis(1-phenyl-1H-tetrazol-5-yl)disulfane;
  1,1'-(2,2'-disulfanediylbis(4-methylthiazole-5,2-diyl))diethanone;
  (NE,N'E)-5,5'-disulfanediylbis(N-benzylidene-1,3,4-thiadiazol-2-amine);
  5,5'-disulfanediylbis(1,3,4-thiadiazole-2-thiol);
  1,2-bis(3-chloro-1,2,4-thiadiazol-5-yl)disulfane;
  1,2-di(1H-pyrazol-4-yl)disulfane;
  4,4'-disulfanediylbis(3-methyl-1-phenyl-1H-pyrazole-5-carbaldehyde);
  1,2-bis(3,5-dimethylisoxazol-4-yl)disulfane;
  tetraethyl 5,5'-disulfanediylbis(3-methylthiophene-2,4-dicarboxylate); and
  5,5'-disulfanediylbis(4H-1,2,4-triazol-3-amine);
or a pharmaceutically acceptable salt thereof.

19. The method of claim 18, where the method is a method of improving tolerance to a low oxygen environment in an individual in need thereof.

20. The method of claim 18, where the method is a method of treating a sickle cell disease or complication resulting from sickle cell disease in an individual in need thereof.

21. The method of claim 18, wherein said contacting comprising administering the compound or salt to said individual.

22. The method of claim 20, wherein the sickle cell disease is selected from sickle cell trait (HbAS), sickle cell anemia (HbSS), sickle cell-hemoglobin C disease (HbSC), sickle cell-hemoglobin E disease, and hemoglobin S-beta-thalassemia.

23. The method of claim 20, wherein the complication resulting from sickle cell disease is sickle cell crisis.

24. The method of claim 20, wherein the complication resulting from sickle cell disease is selected from acute painful episodes, dactylitis, infection, overwhelming post-(auto)splenectomy infection (OPSI), anemia, acute chest syndrome, splenic sequestration, stroke, silent stroke, jaundice, infections, leg ulcers. bone damage, pulmonary hypertension, eye damage, organ failure, priapism, joint pain, cholelithiasis, cholecystitis, avascular necrosis, osteomyelitis, acute papillary necrosis, background retinopathy, proliferative retinopathy, vitreous hemorrhages, retinal detachments, chronic renal failure, sickle cell nephropathy, neurocognitive decline, intracranial and intracerbebral hemorrhage, transient ischemic attacks, infarctive stroke, spinal cord infarction or compression, vestibular dysfunction, sensory hearing loss, growth retardation, delayed puberty, splenic infarction, osteoporosis, bone marrow infarction and necrosis, bone marrow infarction with resulting exacerbation of anemia or pancytopenia, fat embolism, orbital compression syndrome, myocardial infarction, acute heptatic dysfunction, and pregnancy complications of mother or fetus.

* * * * *

UNITED STATES PATENT AND TRADEMARK OFFICE
CERTIFICATE OF CORRECTION

| | | |
|---|---|---|
| PATENT NO. | : 10,758,569 B2 | Page 1 of 2 |
| APPLICATION NO. | : 15/111149 | |
| DATED | : September 1, 2020 | |
| INVENTOR(S) | : Warren M. Zapol et al. | |

It is certified that error appears in the above-identified patent and that said Letters Patent is hereby corrected as shown below:

On the Title Page

Column 1 (Applicants), Lines 2-3, delete "(US); Donald B. Bloch, Boston, MA (US)" and insert -- (US) --

Column 1 (Inventors), Line 2, delete "Kenneth D. Bloch;" and insert -- Kenneth D. Bloch (Deceased), Brookline, MA (US); --

Column 2 (abstract), Line 3, delete "oxygen-being" and insert -- oxygen-binding --

In the Claims

In Column 42, Line 21 (approx.), in Claim 3, after "a" delete "or"

In Column 42, Line 34 (approx.), in Claim 6, delete "leg ulcers." and insert -- leg ulcers, --

In Column 42, Line 40 (approx.), in Claim 6, delete "intracerbebral" and insert -- intracerebral --

In Column 42, Line 48 (approx.), in Claim 6, delete "heptatic" and insert -- hepatic --

In Column 44, Line 18-19 (approx.), in Claim 15, delete "and and" and insert -- and --

In Column 44, Line 22 (approx.), in Claim 15, delete "$NR^s$," and insert -- $NR^5$, --

In Column 45, Line 6-7 (approx.), in Claim 16, delete "and and" and insert -- and --

In Column 46, Line 38, in Claim 24, delete "leg ulcers." and insert -- leg ulcers, --

Signed and Sealed this
Second Day of March, 2021

Drew Hirshfeld
*Performing the Functions and Duties of the
Under Secretary of Commerce for Intellectual Property and
Director of the United States Patent and Trademark Office*

In Column 46, Line 44, in Claim 24, delete "intracerbebral" and insert -- intracerebral --

In Column 46, Line 51, in Claim 24, delete "heptatic" and insert -- hepatic --